United States Patent
Thomson et al.

(10) Patent No.: US 10,081,792 B2
(45) Date of Patent: Sep. 25, 2018

(54) DERIVATION OF HUMAN MICROGLIA FROM PLURIPOTENT STEM CELLS

(71) Applicant: Wisconsin Alumni Research Foundation, Madison, WI (US)

(72) Inventors: James A. Thomson, Madison, WI (US); Nicholas E. Propson, Houston, TX (US); Michael P. Schwartz, Madison, WI (US); Zhonggang Hou, Madison, WI (US); Gene I. Uenishi, Madison, WI (US); Igor I. Slukvin, Verona, WI (US); William L. Murphy, Waunakee, WI (US); Jue Zhang, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 14/986,224

(22) Filed: Dec. 31, 2015

(65) Prior Publication Data

US 2016/0186137 A1    Jun. 30, 2016

Related U.S. Application Data

(60) Provisional application No. 62/098,824, filed on Dec. 31, 2014.

(51) Int. Cl.
| | |
|---|---|
| *C12N 5/00* | (2006.01) |
| *C12N 5/02* | (2006.01) |
| *C12N 5/071* | (2010.01) |
| *C12N 5/079* | (2010.01) |
| *C12N 5/0789* | (2010.01) |
| *G01N 33/50* | (2006.01) |
| *C12N 5/0786* | (2010.01) |

(52) U.S. Cl.
CPC ......... *C12N 5/0622* (2013.01); *C12N 5/0645* (2013.01); *C12N 5/0647* (2013.01); *C12N 5/0697* (2013.01); *G01N 33/5014* (2013.01); *G01N 33/5058* (2013.01); *C12N 5/0062* (2013.01); *C12N 5/0068* (2013.01); *C12N 2500/25* (2013.01); *C12N 2501/115* (2013.01); *C12N 2501/15* (2013.01); *C12N 2501/22* (2013.01); *C12N 2501/999* (2013.01); *C12N 2506/02* (2013.01); *C12N 2513/00* (2013.01)

(58) Field of Classification Search
CPC .. C12N 5/0062; C12N 5/0068; C12N 5/0622; C12N 5/0647; C12N 2501/15; C12N 2501/115; C12N 2501/999; C12N 2506/02
USPC ................. 435/377, 372, 395, 405
See application file for complete search history.

(56) References Cited

PUBLICATIONS

Bellin et al., 2012, Nature reviews/Molecular Cell Biology, vol. 13, p. 713-726.*
Wang, Yigang, 2014, New Journal of Science, vol. 2014, Article ID 756240, pp. 1-22.*
Narsinh et al., 2011, Molecular therapy, vol. 9, No. 4, p. 635-638.*
Burridge et al., 2011, PLoS ONE, vol. 6, No. 4, e18293, p. 1-16.*
Ader, et al., Modeling human development in 3D culture, Curr. Opin. Cell Biol. 31, 23-8 (2014).
Arnold, et al., The importance of microglia in the development of the vasculature in the central nervous system, Vasc Cell. Feb. 19, 2013;5(1):4.
Balmer, et al., Epigenetics and transcriptomics to detect adverse drug effects in model systems of human development, Basic Clin. Pharmacol. Toxicol. 115, 59 (Jul. 2014).
Bellinger, A strategy for comparing the contributions of environmental chemicals and other risk factors to neurodevelopment of children, Environ. Health Perspect. 120, 501-7 (Apr. 2012).
Brustle, et al., Embryonic stem cell-derived glial precursors: a source of myelinating transplants, Science 285, 754 (Jul. 30, 1999).
Bystron, et al., The first neurons of the human cerebral cortex, Nat Neurosci 9, 880-6 (2006).
Bystron, et al., Development of the human cerebral cortex: Boulder Committee revisited, Nat. Rev. Neurosci. 9, 110-22 (Feb. 2008).
Chambers, et al., Highly efficient neural conversion of human ES and iPS cells by dual inhibition of SMAD signaling, Nat. Biotechnol. 27, 275-80 (Mar. 2009).
Chen, et al., Chemically defined conditions for human iPSC derivation and culture, Nat. Methods 8, 424-9 (May 2011).
Cortes, et al., Support-vector networks, Mach. Learn. 20, 273 (Sep. 1995).
Dominguez, et al., POU-III transcription factors (Brn1, Brn2, and Oct6) influence neurogenesis, molecular identity, and migratory destination of upper-layer cells of the cerebral cortex, Cereb. Cortex 23, 2632 (Nov. 2013).
Eiraku, et al., Self-organized formation of polarized cortical tissues from ESCs and its active manipulation by extrinsic signals, Cell Stem Cell 3, 519 (Nov. 2008).
Furey, et al., Support vector machine classification and validation of cancer tissue samples using microarray expression data, Bioinformatics 16, 906 (Oct. 2000).
Ginhoux et al., Fate mapping analysis reveals that adult microglia derive from primitive macrophages, Science 330 (6005):841-5 (2010).
Ginhoux, et al., Origin and differentiation of microglia, Front Cell Neurosci. Apr. 17, 2013;7:45.
Giulian et al., Cell surface morphology identifies microglia as a distinct class of mononuclear phagocyte, J. Neurosci. 15(11):7712-7726 (1995).

(Continued)

*Primary Examiner* — Shin Lin Chen
(74) *Attorney, Agent, or Firm* — Quarles & Brady LLP

(57) ABSTRACT

The present invention relates to methods for deriving human hematopoietic progenitors, primitive macrophages, and microglial cells from human pluripotent stem cells. In particular, provided herein are highly efficient and reproducible methods of obtaining human primitive macrophages and microglia from human pluripotent stem cells, where the primitive macrophages and microglia can be suitable for clinically relevant therapeutic applications.

7 Claims, 17 Drawing Sheets
(16 of 17 Drawing Sheet(s) Filed in Color)
Specification includes a Sequence Listing.

(56) References Cited

PUBLICATIONS

Golub, et al., Molecular classification of cancer: class discovery and class prediction by gene expression monitoring, Science 286, 531-7 (Oct. 1999).

Grandjean, et al., Developmental neurotoxicity of industrial chemicals, Lancet 368, 2167 (Dec. 2006).

Hansen, et al., Non-epithelial stem cells and cortical interneuron production in the human ganglionic eminences, Nat. Neurosci. 16, 1576-87 (Nov. 2013).

Hou, et al., A human pluripotent stem cell platform for assessing developmental neural toxicity screening, Stem Cell Res. Ther. 4, S12 (Dec. 2013).

James, et al., Neuronal action on the developing blood vessel pattern, Semin. Cell Dev. Biol. 22, 1019-27 (2011).

Kadoshima, et al., Self-organization of axial polarity, inside-out layer pattern, and species-specific progenitor dynamics in human ES cell-derived neocortex, Proc. Natl. Acad. Sci. U. S. A. 110, 20284-9 (Dec. 2013).

Kettenmann, et al., Physiology of microglia, Physiol. Rev. 91, 461-553 (Apr. 2011).

Kleinstreuer, et al., Phenotypic screening of the ToxCast chemical library to classify toxic and therapeutic mechanisms, Nat. Biotechnol. 32, 583-91 (Jun. 2014).

Lancaster, et al., Cerebral organoids model human brain development and microcephaly, Nature 501, 373-9 (Sep. 2013).

Langmead, et al., Ultrafast and memory-efficient alignment of short DNA sequences to the human genome, Genome Biol. 10(3), R25 (2009).

Li, et al., RSEM:accurate transcript quantification from RNA-Seq data with or without a reference genome, BMC Bioinformatics 12, 323 (2011).

Li, et al., Coordination of sonic hedgehog and Wnt signaling determines ventral and dorsal telencephalic neuron types from human embryonic stem cells, Development 136, 4055 (Dec. 2009).

Lui, et al., Development and evolution of the human neocortex, Cell 146, 18 (Jul. 2011).

Mariani, et al., Modeling human cortical development in vitro using induced pluripotent stem cells, Proc Natl Acad Sci U S A. Jul. 31, 2012;109(31):12770-5.

Marin-Padilla, et al., Developmental aspects of the intracerebral microvasculature and perivascular spaces: insights into brain response to late-life diseases, J. Neuropathol. Exp. Neurol. 70, 1060 (Dec. 2011).

Marin-Padilla, The human brain intracerebral microvascular system: development and structure, Front. Neuroanat. 6 (Sep. 13, 2012).

Meyer, et al., Embryonic and early fetal development of the human neocortex, J. Neurosci. 20, 1858 (Mar. 2000).

Molyneaux, et al., Neuronal subtype specification in the cerebral cortex, Nat. Rev. Neurosci. 8, 427 (Jun. 2007).

Monier, et al., Distribution and differentiation of microglia in the human encephalon during the first two trimesters of gestation, J. Comp. Neurol. 499, 565-82 (Dec. 2006).

Monier, et al., Entry and distribution of microglial cells in human embryonic and fetal cerebral cortex, J. Neuropathol. Exp. Neurol. 66, 372 (May 2007).

Moors, et al., Human neurospheres as three-dimensional cellular systems for developmental neurotoxicity testing, Environ. Health Perspect. 117, 1131-8 (Jul. 2009).

Needham, et al., Partition of environmental chemicals between maternal and fetal blood and tissues, Environ. Sci. Technol. 45, 1121-6 (Feb. 2011).

Olson, et al., Concordance of the toxicity of pharmaceuticals in humans and in animals, Regulatory Toxicology and Pharmacology 32, 56-67 (2000).

Rakic, Developmental and evolutionary adaptations of cortical radial glia, Cereb. Cortex 13, 541-9 (Jun. 2003).

Rakic, et al., Emerging complexity of layer I in human cerebral cortex, Cereb. Cortex 13, 1072-83 (Oct. 2003).

Rakic, Evolution of the neocortex: a perspective from developmental biology, Nat. Rev. Neurosci. 10, 724-35 (Oct. 2009).

Rice, et al., Critical periods of vulnerability for the developing nervous system: evidence from humans and animal models, Environ. Health Perspect. 108, 511-33 (Jun. 2000).

Singec, et al., Defining the actual sensitivity and specificity of the neurosphere assay in stem cell biology, Nat. Methods 3, 801-6 (Oct. 2006).

Slukvin, et al.,Directed differentiation of human embryonic stem cells into functional dendritic cells through the myeloid pathway, J Immunol. Mar. 1, 2006;176(5):2924-32.

Smirnova, et al., Developmental neurotoxicity—challenges in the 21st century and in vitro opportunities, ALTEX-Altern. Anim. Exp. 31, 129 (2014).

Stolp, et al., The Long and the Short of it: Gene and Environment Interactions During Early Cortical Development and Consequences for Long-Term Neurological Disease, Front. Psychiatry 3 (2012).

Struyf, et al., Combining gene expression, demographic and clinical data in modeling disease: a case study of bipolar disorder and schizophrenia, BMC Genomics 9, 531 (Nov. 2008).

Takahashi, et al., Induction of pluripotent stem cells from adult human fibroblasts by defined factors, Cell 131, 861-72 (Nov. 2007).

Thomson et al., Embryonic stem cell lines derived from human blastocysts, Science 282:1145-1147 (1998).

Uenishi, et al. Tenascin C promotes hematoendothelial development and T lymphoid commitment from human pluripotent stem cells in chemically defined conditions, Stem Cell Rep 3(6):1073-1084, 2014.

Vapnik, Statistical Learning Theory (Wiley, New York, 1998), pp. 736.

Verney, et al., Early microglial colonization of the human forebrain and possible involvement in periventricular white-matter injury of preterm infants, J. Anat. 217, 436 (Oct. 2010).

Vodyanik, et al., Leukosialin (CD43) defines hematopoietic progenitors in human embryonic stem cell differentiation cultures, Blood (2006) 108:2095-2105.

Wilson, et al., Multiparametric High Content Analysis for assessment of neurotoxicity in differentiated neuronal cell lines and human embryonic stem cell-derived neurons, Neurotoxicology 42, 33 (May 2014).

Yu et al., Induced pluripotent stem cell lines derived from human somatic cells, Science 318:1917-1920 (2007).

Zecevic, et al., Early development and composition of the human primordial plexiform layer: An immunohistochemical study, The Journal of Comparative Neurology 412, 241-54 (1999).

Zhang, et al., In vitro differentiation of transplantable neural precursors from human embryonic stem cells, Nat. Biotechnol. 19, 1129-33 (Dec. 2001).

* cited by examiner

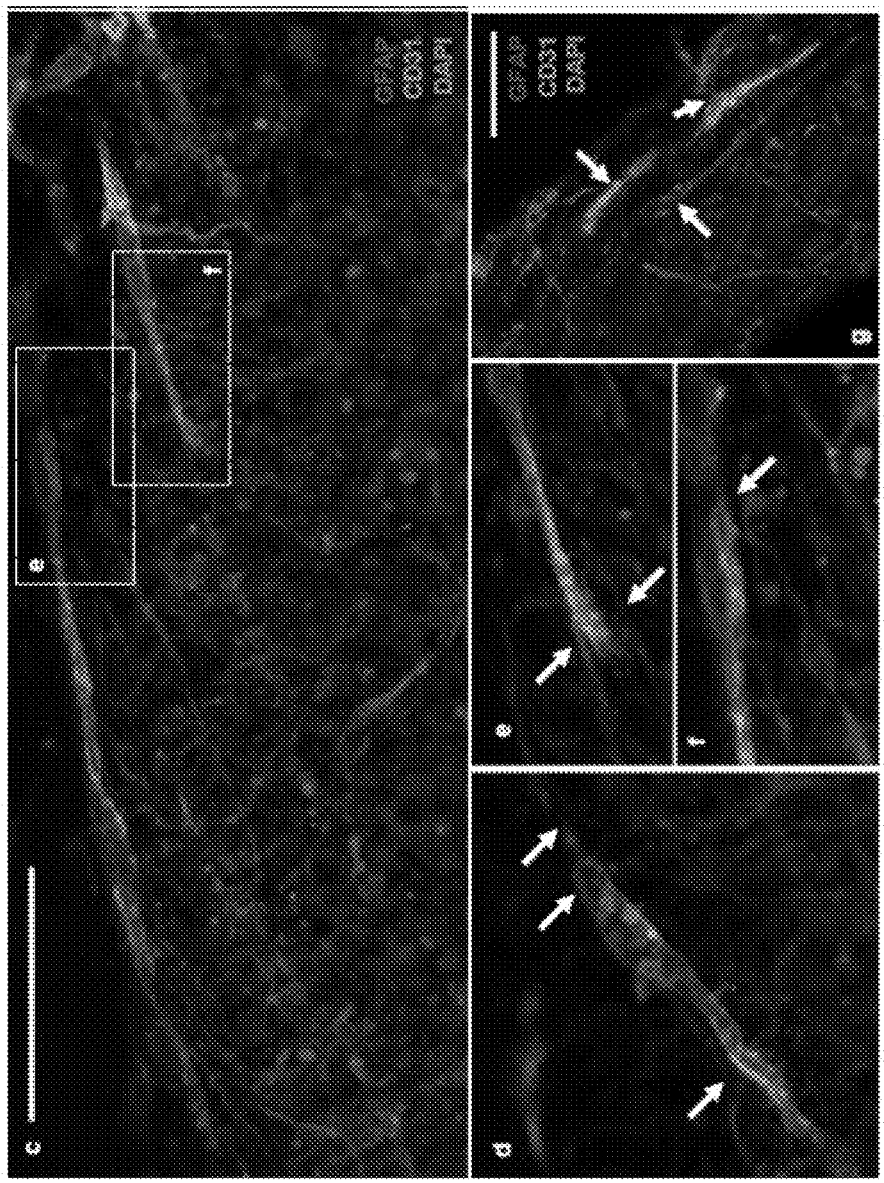
FIGS. 2A-2G, CONTINUED

FIGS. 3A-3D

| A. Microglia gene expression | | Day 16 | Day 21 |
|---|---|---|---|
| AIF1/IBA1 | Allograft inflammatory factor 1 | 12.1±3.3 | 15.6±8.8 |
| TREM2 | triggering receptor expressed on myeloid cells 2 | 6.7 ± 2.2 | 7.0 ± 5.0 |
| ITGAM/CD11b | Integrin alpha M | 2.3±0.6 | 1.2±1.2 |
| PTPRC/CD45 | Protein tyrosine phosphatase, receptor type, C | 4.1±0.9 | 3.6±3.3 |
| CX3CR1 | CX3C chemokine receptor 1 | 3.8±0.8 | 3.7±4.6 |
| CD68 | Cluster of Differentiation 68 | 17.3±4.0 | 23.8±18.9 |
| CD14 | Cluster of Differentiation 14 | 1.8±1.6 | 3.0±1.4 |
| Normalized expression (Avg. TPM ± S.D.; N = 4) | | | |

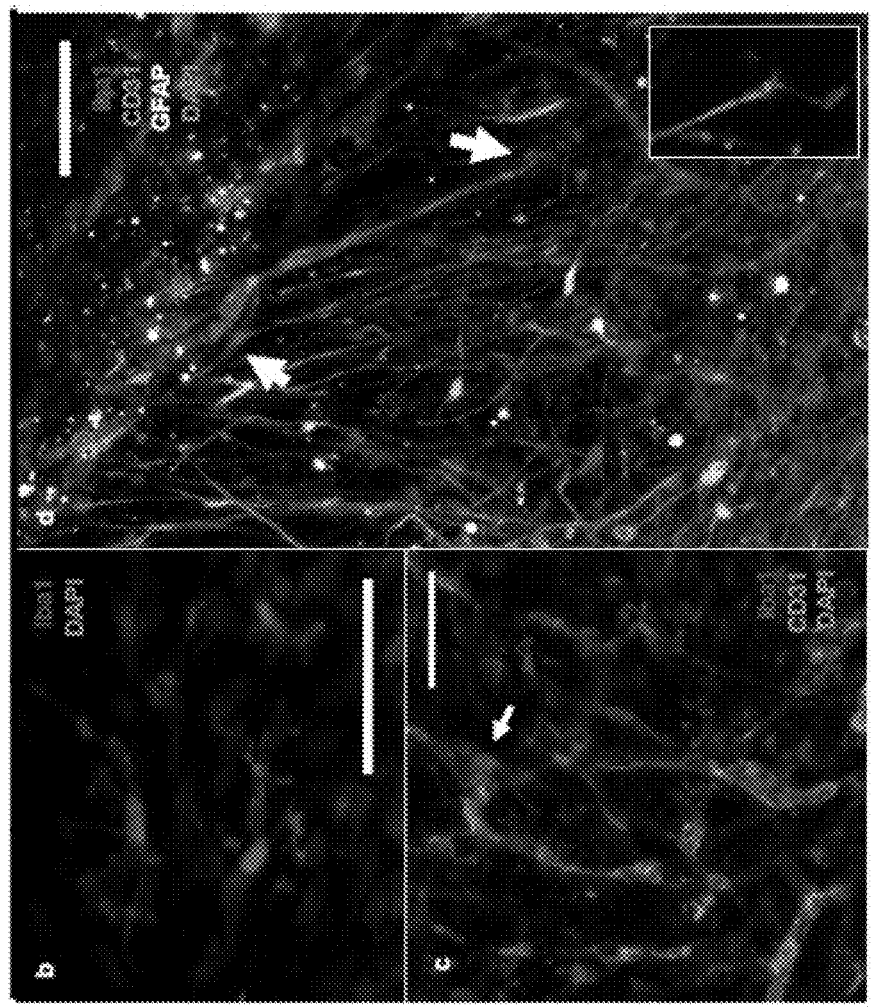
FIGS. 3A-3D, CONTINUED

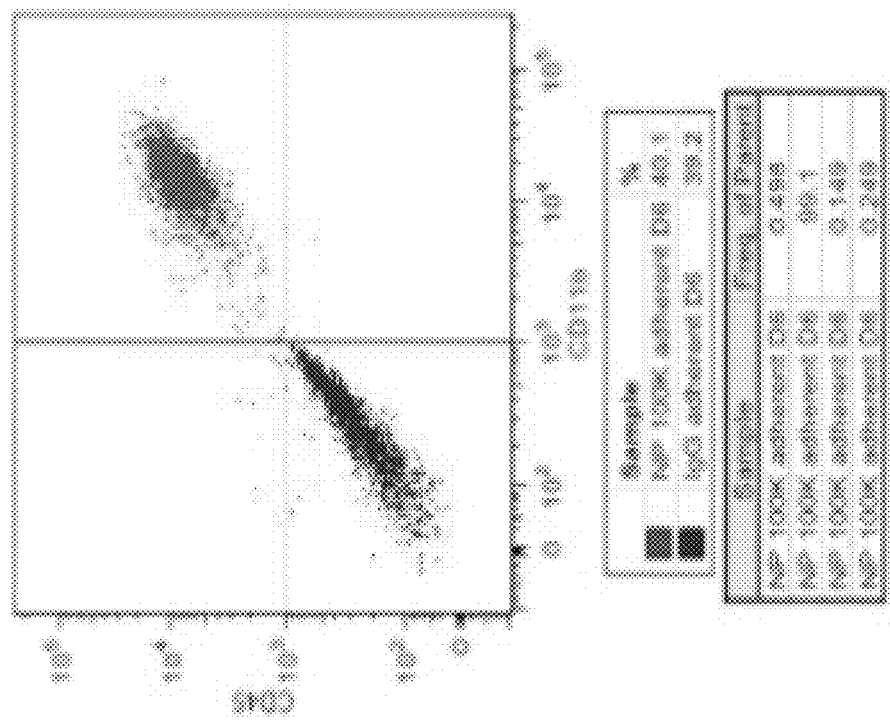
FIGS. 4A-4B, CONTINUED

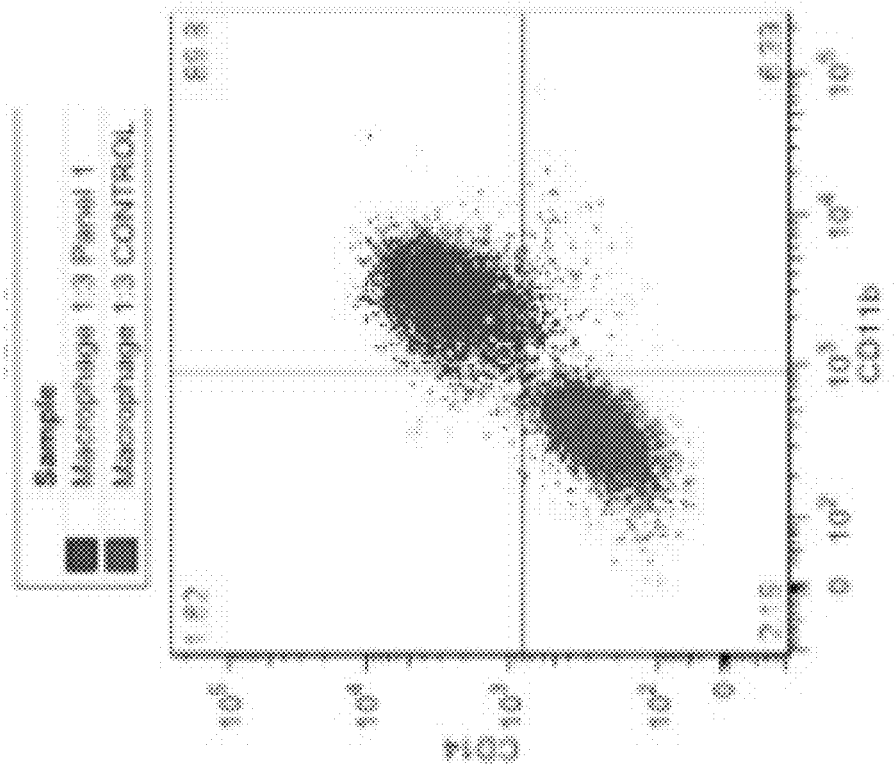
FIGS. 6A-6D, CONTINUED

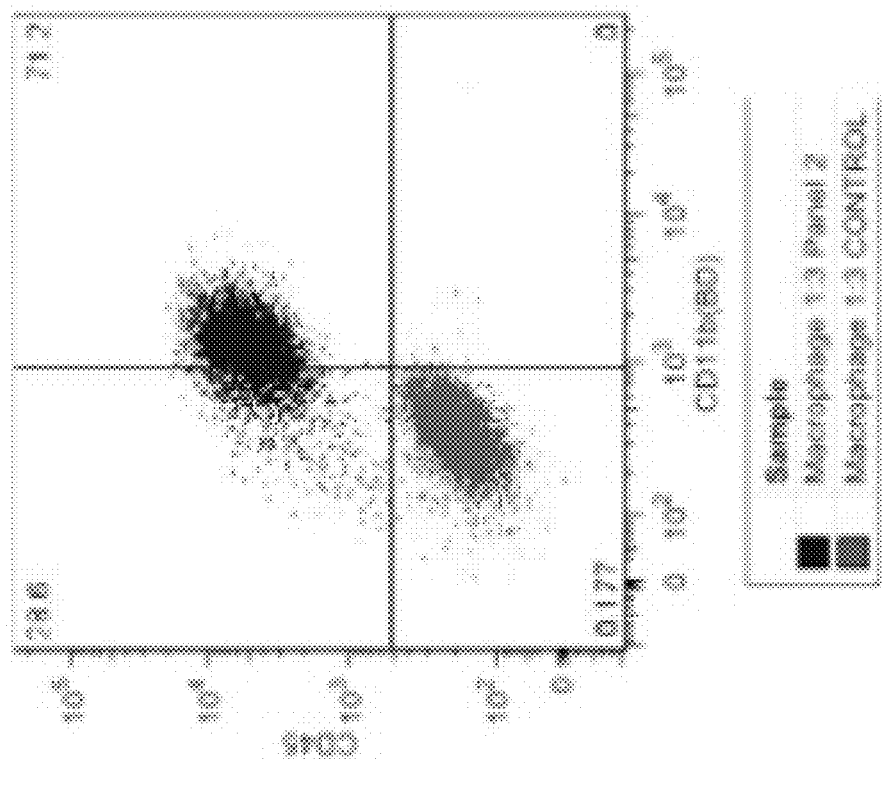
FIGS. 6A-6D, CONTINUED

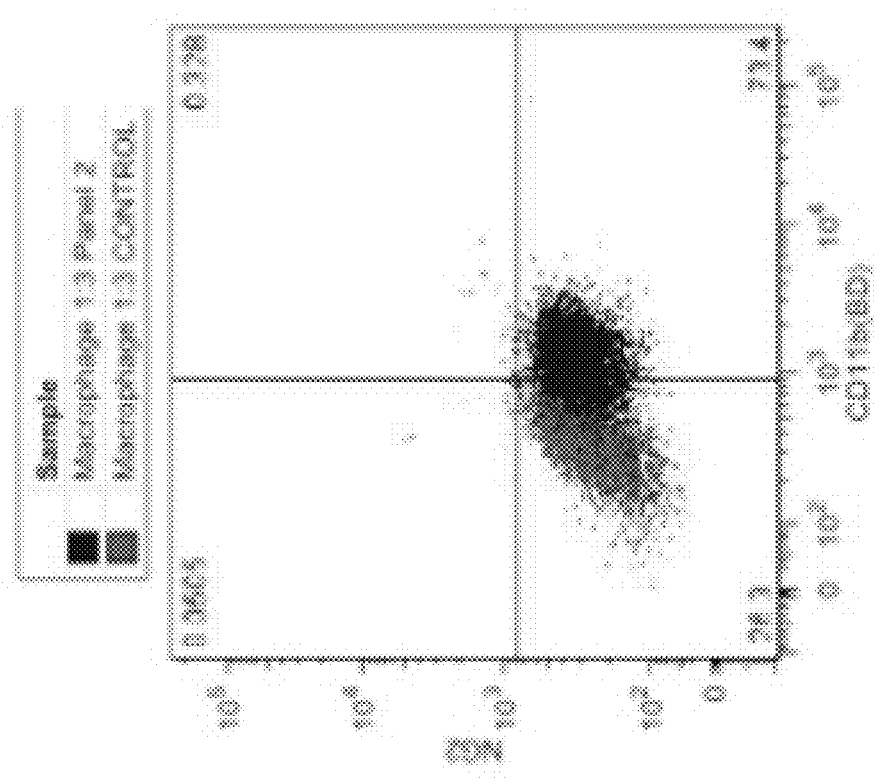
FIGS. 6A-6D, CONTINUED

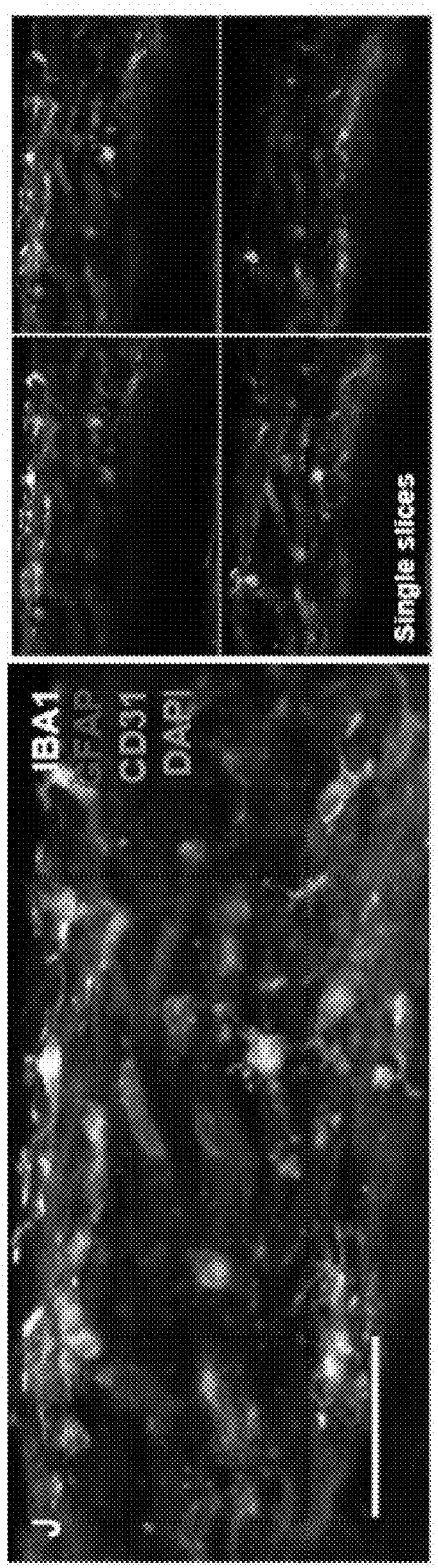
FIGS. 7A-7J, CONTINUED

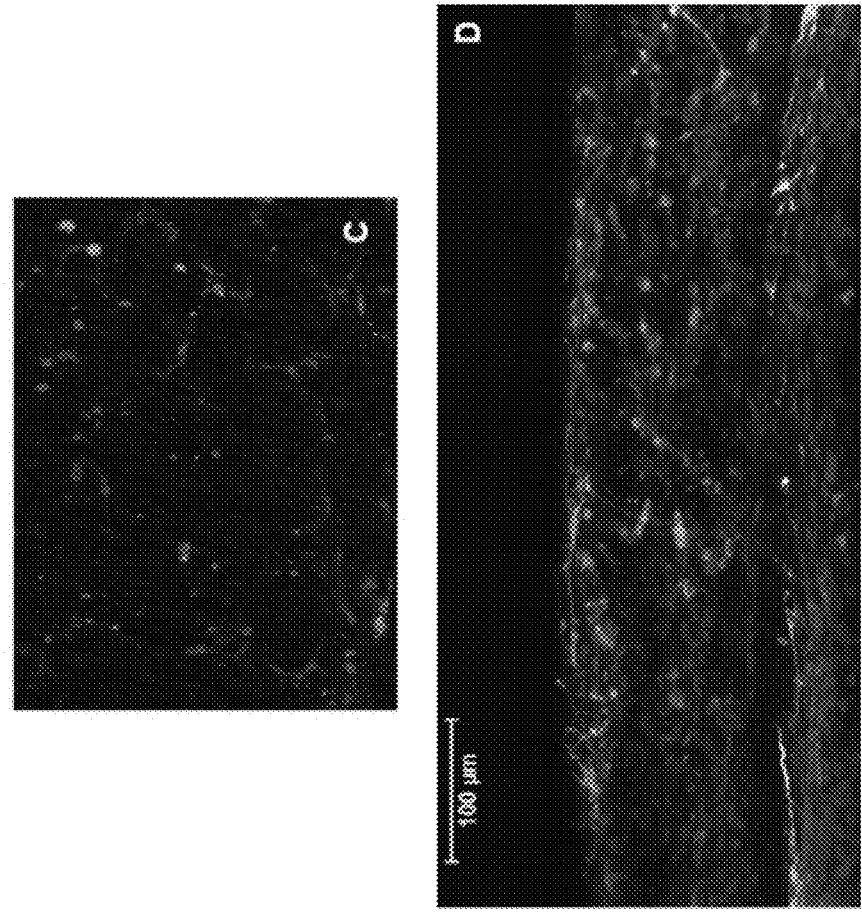
FIGS. 8A-8D, CONTINUED

DERIVATION OF HUMAN MICROGLIA FROM PLURIPOTENT STEM CELLS

CROSS-REFERENCE TO RELATED APPLICATIONS

This application claims the benefit of U.S. Application Ser. No. 62/098,824, filed Dec. 31, 2014, which is incorporated herein as if set forth in its entirety.

STATEMENT REGARDING FEDERALLY FUNDED RESEARCH OR DEVELOPMENT

This invention was made with government support under TR000506 awarded by the National Institutes of Health. The government has certain rights in the invention.

BACKGROUND

Pluripotent stem cells offer a potentially powerful tool for improving in vitro models and investigating the underlying mechanisms of development of human neural tissue and of neurotoxicity. Animal models have provided insight into these mechanisms, but are of limited value for predicting developmental neurotoxicity due to poorly understood differences in the human brain such as an expanded cerebral cortex. There exists substantial academic literature supporting the theory that microglia arise from the transition of a primitive myeloid progenitor cell population during early development. As the neural tube begins to form, it has been shown in rodent models that early yolk sac hematopoietic progenitors begin to migrate to the anterior position of the neural tube and form resident populations of immune-like cells that later develop into microglia. The majority of studies have been performed in rodent models, leaving much to be desired for the study of the human cell type. Accordingly, there remains a need in the art, for efficient, reproducible, and xenogeneic material-free methods for differentiating human pluripotent stem cells into microglia suitable for clinical cell therapies and for predictive analysis of candidate neurotoxic agents.

SUMMARY OF THE INVENTION

In a first aspect, this document provides a method of obtaining human hematopoietic precursor cells. The method generally comprises culturing human pluripotent stem cells under normoxic conditions for about 24 hours, where the pluripotent stem cells are cultured on a substrate that promotes cell adhesion and in a culture medium consisting essentially of L-ascorbic acid-2-phosphate magnesium, sodium selenium, transferrin, insulin, $NaHCO_3$, fibroblast growth factor 2 (FGF2), transforming growth factor beta 1 (TGFβ1), and a Rho kinase (ROCK) inhibitor, whereby the cultured pluripotent stem cells differentiate into hematopoietic precursor cells (HPCs). The substrate that promotes cell adhesion can comprise Tenascin-C. The Tenascin-C can be recombinant human Tenascin-C. The ROCK inhibitor can be selected from the group consisting of Y-27632, Blebbistatin, HA-1077.

In another aspect, this document provides a method of obtaining human myeloid progenitors. The method generally comprises culturing human HPCs obtained according to a method provided herein for about 3 to about 5 days in a culture medium comprising FGF2, a vascular endothelium growth factor (VEGF), thrombopoietin (TPO), stem cell factor (SCF), interleukin-6 (IL-6), and interleukin-3 (IL-3), where the hematopoietic progenitor cells differentiate into myeloid progenitors.

In yet another aspect, provided herein is a method of obtaining human primitive macrophages. The method generally comprises culturing human myeloid progenitors obtained according to a method provided herein in the presence of a culture medium comprising insulin and a hematopoietic cytokine, whereby the cultured myeloid progenitors differentiate into a cell population comprising at least 80% $CD45^+/CD11b^+/CD14^+$ primitive macrophages. The $CD45^+/CD11b^+/CD14^+$ primitive macrophages can be $CD34^{low/negative}$. In some cases, the $CD45^+/CD11b^+/CD14^+$ primitive macrophages do not express a detectable level of Iba-1. The hematopoietic cytokine can be granulocyte macrophage colony-stimulating factor (GM-CSF).

In another aspect, this document provides a method of obtaining human hematopoietic precursor cells. Generally, the method comprises the steps of (a) culturing human pluripotent stem cells under hypoxic conditions on a substrate that promotes cell adhesion and in a growth medium consisting essentially of Dulbecco's Modified Eagle Medium (DMEM), nutrient mixture F12, a chemically defined lipid concentrate, L-ascorbic acid-2-phosphate magnesium, monothioglycerol, sodium selenium, polyvinyl alcohol, L-alanyl-L-glutamine, FGF2, bone morphogenetic protein 4 (BMP4), Activin A, and an inhibitor of glycogen synthase 3 (GSK3) for a length of time between about 40 and about 48 hours, where the pluripotent stem cells are initially seeded on the substrate at a cell density between about $2 \times 10^5$ cells per $cm^2$ and about $2.5 \times 10^5$ cells per $cm^2$; and (b) further culturing the cultured cells of step (a) under hypoxic conditions in a culture medium comprising FGF2, a VEGF, and an inhibitor of TGFβ-mediated signaling, whereby the further cultured cells differentiate into hematopoietic progenitor cells. The substrate that promotes cell adhesion can comprise vitronectin. The inhibitor of GSK3 can be selected from the group consisting of CHIR99021, lithium chloride (LiCl), and 6-bromoindirubin-3'-oxime (BIO). The inhibitor of TGFβ-mediated signaling can be selected from the group consisting of SB431542 and A-83-01.

In a further aspect, provided herein is a method of obtaining human myeloid progenitors. The method generally comprises culturing human HPCs obtained according to a method provided herein under normoxic conditions in a culture medium comprising FGF2, a VEGF, TPO, SCF, IL-6, and IL-3 until cultured hematopoietic progenitor cells differentiate into myeloid progenitors.

In another aspect, this document provides a method of obtaining human primitive macrophages. The method generally comprises culturing human myeloid progenitors obtained according to a method provided herein under normoxic conditions in the presence of a culture medium comprising insulin and a hematopoietic cytokine, whereby the cultured myeloid progenitors differentiate into a cell population comprising at least 80% $CD45^+/CD11b^+/CD14^+$ primitive macrophages. The hematopoietic cytokine can be human granulocyte macrophage colony-stimulating factor (GM-CSF). The $CD45^+/CD11b^+/CD14^+$ primitive macrophages can be $CD34^{low/negative}$. In some cases, the $CD45^+/CD11b^+/CD14^+$ primitive macrophages do not express a detectable level of Iba-1.

In another aspect, this document provides a method of making a composition comprising human microglial cells, the method comprising contacting human pluripotent stem cell-derived primitive macrophages to a chemically defined, xenogen-free three-dimensional tissue construct comprising stratified layers of human neurons and glia, thereby producing a composition comprising human microglial cells. The primitive macrophages can be obtained according to a method described herein. The tissue construct can comprise a hydrogel. The microglial cells can be Iba-1$^+$. Prior to the contacting step, the human primitive macrophages can be cultured for about 5 days in a culture medium consisting essentially of DMEM/F12, interleukin-1-beta (IL-1β), serum, and a hematopoietic growth factor. The hematopoietic growth factor can be macrophage colony-stimulating factor (M-CSF).

In yet another aspect, this document provides a method of screening a compound for toxicity. Generally, the method comprises exposing a test compound to a composition obtained according to a method provided herein and assaying for an effect of the compound on one or more aspects of human microglial growth or development.

These and other features, objects, and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the claims recited herein for interpreting the scope of the invention.

INCORPORATION BY REFERENCE

All publications, patents, and patent applications mentioned in this specification are herein incorporated by reference in their entirety as if each individual publication, patent, and patent application was specifically and individually indicated to be incorporated by reference.

This application includes a sequence listing in computer readable form (a "txt" file) that is submitted herewith. This sequence listing is incorporated by reference herein.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

The present invention will be better understood and features, aspects and advantages other than those set forth above will become apparent when consideration is given to the following detailed description thereof. Such detailed description makes reference to the following drawings, wherein:

FIGS. 3A-3D depict microglia marker expression patterns, ramified morphology, and capillary tubule interactions of microglia/macrophage precursors. (A) Expression of microglia markers within neural constructs at days 16 and 21. Values shown are average transcripts per million (TPM) for control constructs from toxicity experiment ±S.D. (N=4). (B, C) Immunofluorescence images illustrating microglia (Iba1, red), endothelial cells (CD31, green), glial cells (GFAP, white), and nuclei (DAPI, blue): (B) Microglia (Iba1, red) with ramified morphologies; (C) Microglia (Iba1, red) interacting with endothelial cells (CD31, green); (D) Microglia (red), endothelial cells (green), and glial cells (white) at the leading edge of an extending capillary tubule. Inset illustrates a projection image for fewer slices and without GFAP to highlight interactions of Iba+ microglia with the extending tubule. Scale bars: 50 μm.

DETAILED DESCRIPTION OF THE INVENTION

Figures 1A, 1B:
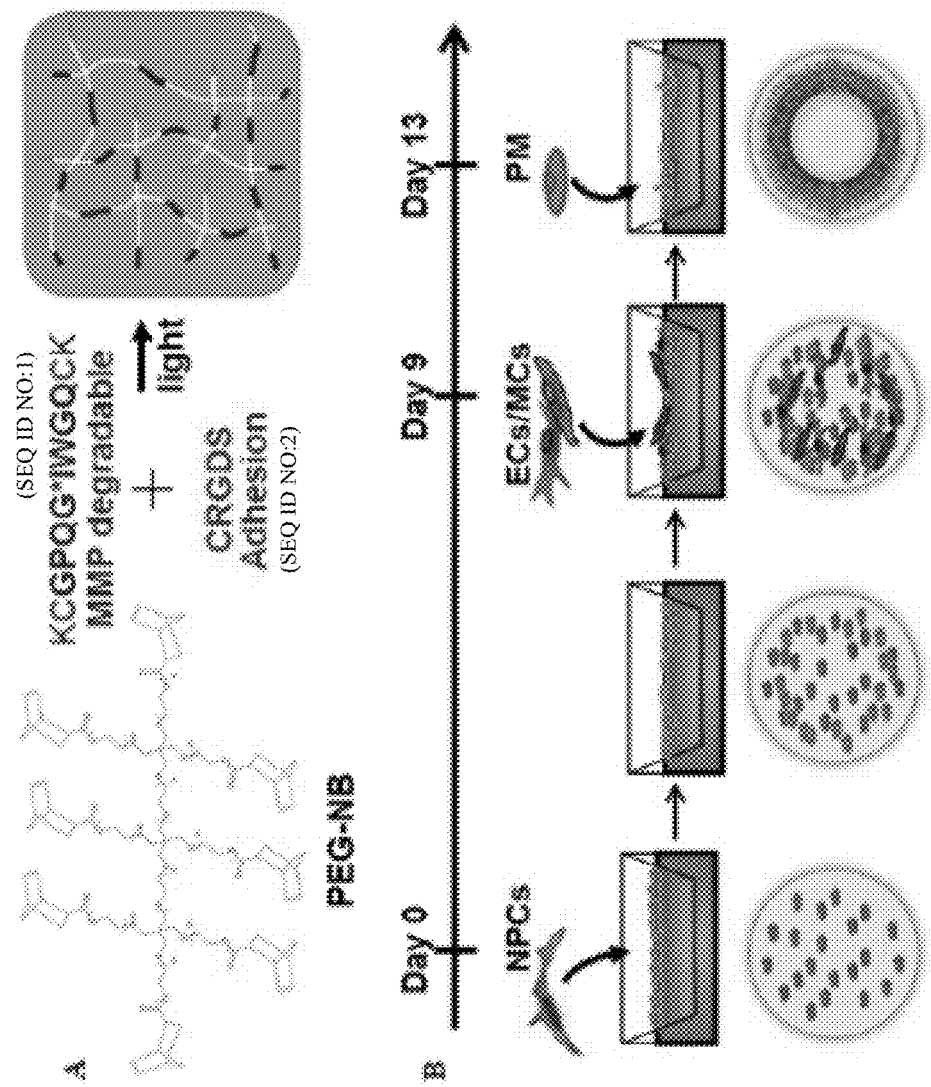
FIGS. 1A-1B depict neural construct formation on synthetic poly(ethylene glycol) hydrogels. (A) Hydrogels were formed using "thiol-ene" photopolymerization to crosslink 8-arm poly(ethylene glycol)-norbornene (PEG-NB) molecules with cysteine-flanked matrix metalloproteinase (MMP)-degradable peptides, while pendant CRGDS peptides were incorporated for adhesion. (B) Human embryonic stem cell-derived precursor cells were cocultured on PEG hydrogels in 24-well transwell inserts. Neural progenitor cells (NPCs) were seeded on synthetic PEG hydrogels (Day 0), followed by endothelial cells (ECs) and mesenchymal stem cells (MSCs) at Day 9 and microglia/macrophage precursors (MG) at day 13.
Figures 2A, 2B, 2C, 2D, 2E, 2F, 2G:
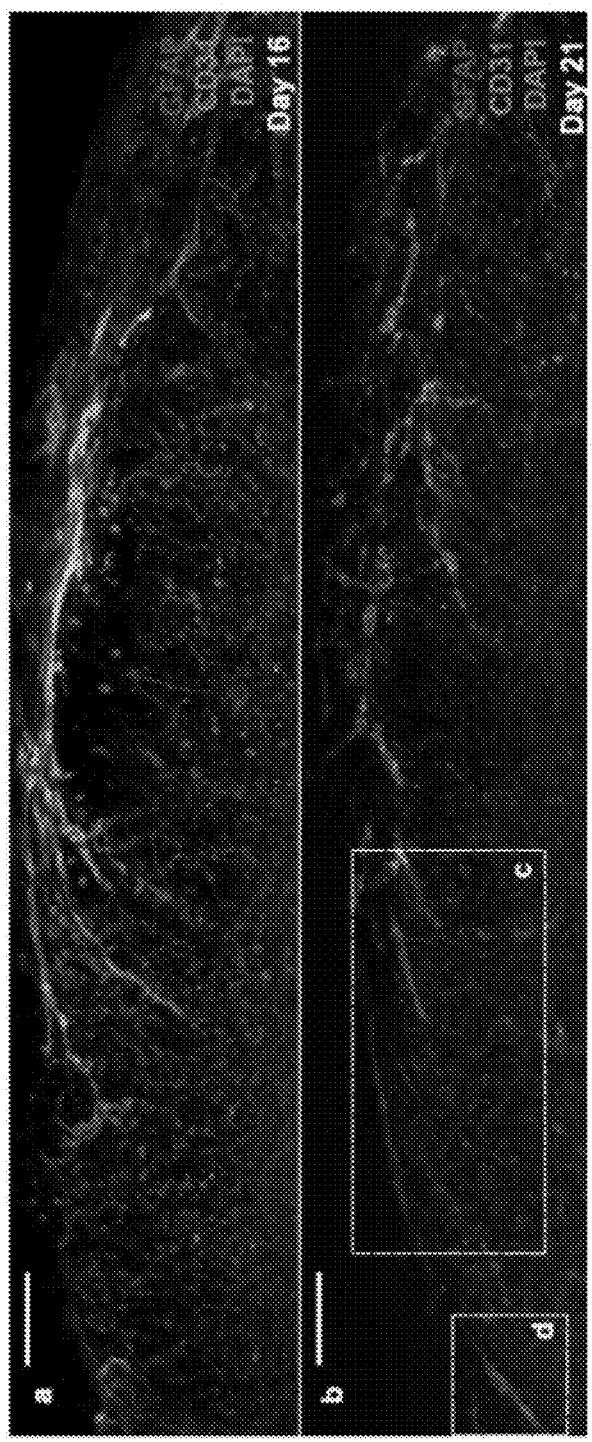
FIGS. 2A-2G depict capillary networks and microglia within three-dimensional neural tissue constructs. Immunofluorescence was detected using antibodies specific for endothelial cells (CD31, green), glial cells (GFAP, red), and nuclei (DAPI, blue). Maximum projection z-stacks for neural constructs at (A) day 1 and (B-G) day 21. Magnified portions of (B) are shown in (C) and (D) as labeled. Magnified regions of (C) are shown in (E) and (F) as labeled. All images: Arrows show associations between CD31$^+$ endothelial cells and GFAP$^+$ glial cells. Scale bars: (A-C) 100 μm; (D) 50×50 μm; (E-F) 25×50 μm; (G) 50 μm.
Figures 4A, 4B:
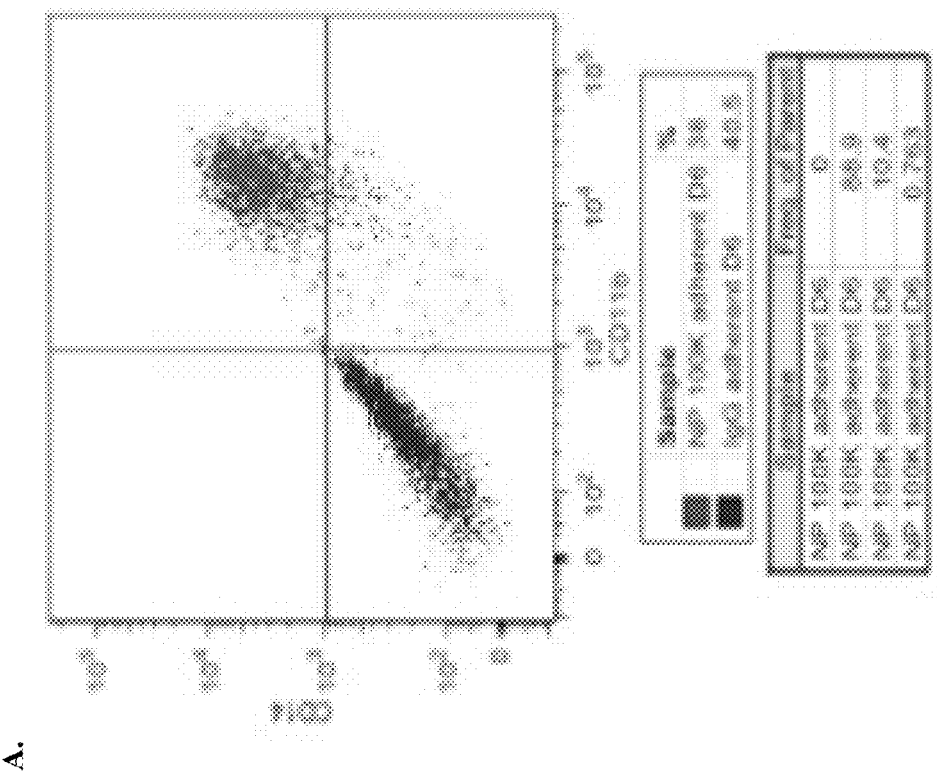
FIGS. 4A-4B present flow cytometry data from human pluripotent stem cell-derived primitive macrophages (day 6). Quadrants depict (A) CD14 and CD11b expression and (B) CD45 and CD11b expression.
Figures 5A, 5B:
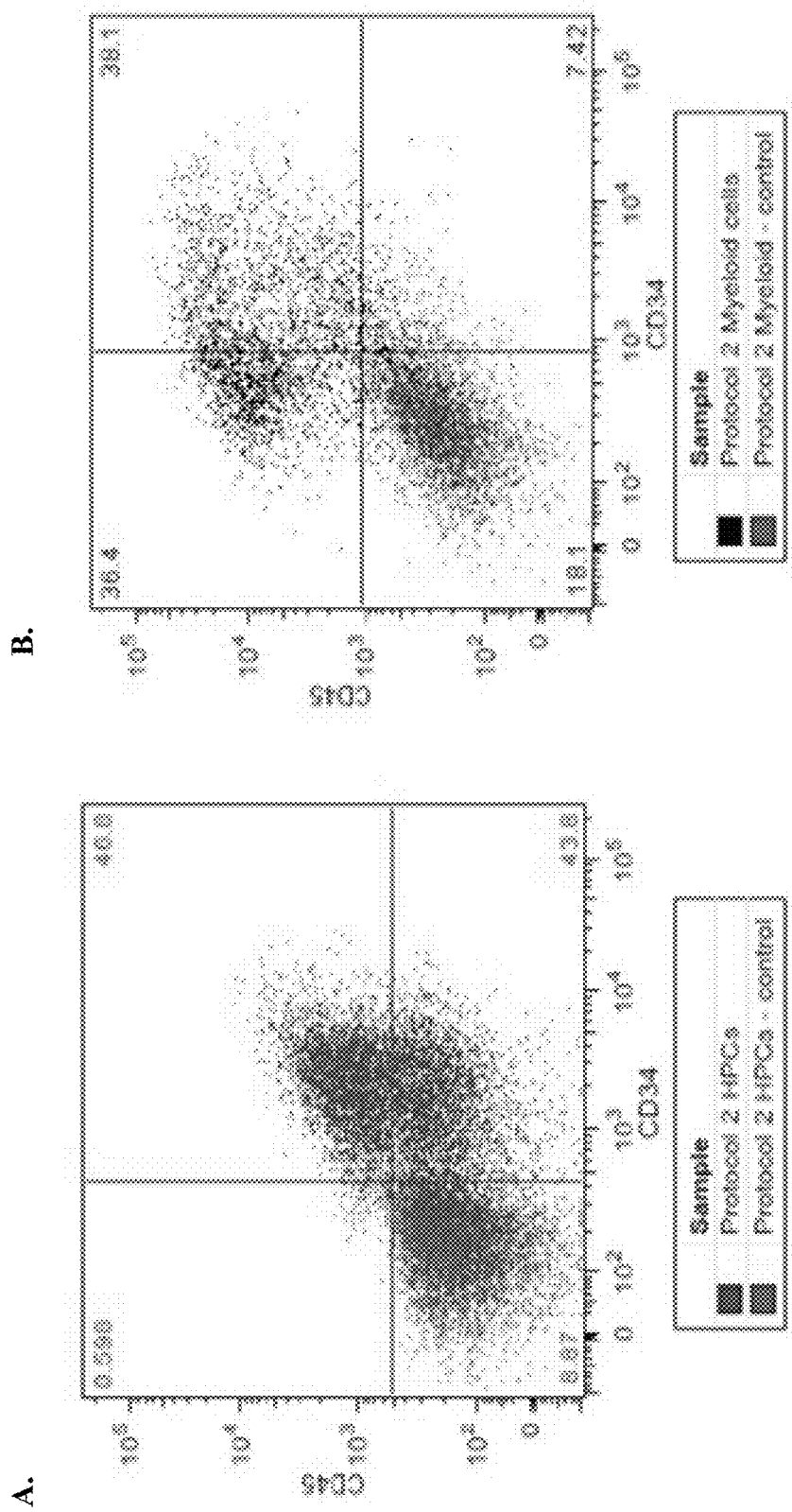
FIGS. 5A-5B present flow cytometry data from hematopoietic precursor cells (HPCs) and myeloid precursors. Quadrants depict (A) CD14 and CD34 expression and (B) CD45 and CD34 expression.
Figures 6A, 6B, 6C, 6D:
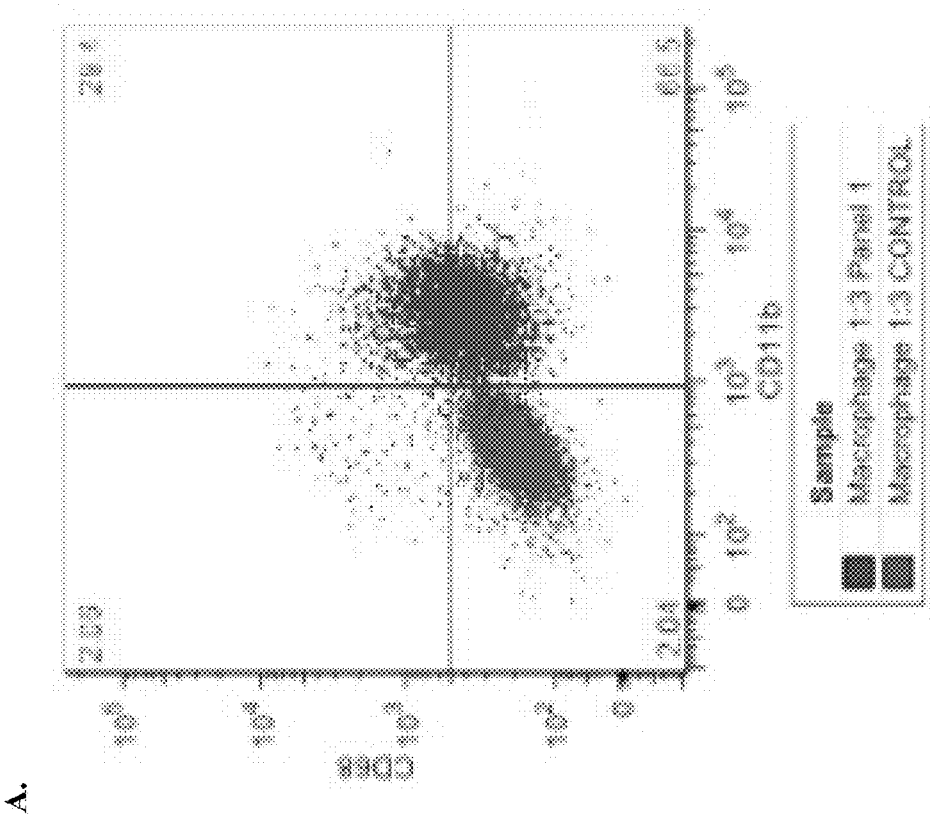
FIGS. 6A-6D present flow cytometry data characterizing human pluripotent stem cell-derived primitive macrophages. Quadrants depict (A) CD68 and CD11b expression; (B) CD14 and CD11b expression; (C) CD45 and CD11b; and (D) NG2 and CD11b.
Figures 7A, 7B, 7C, 7D, 7E, 7F, 7G, 7H, 7I, 7J:
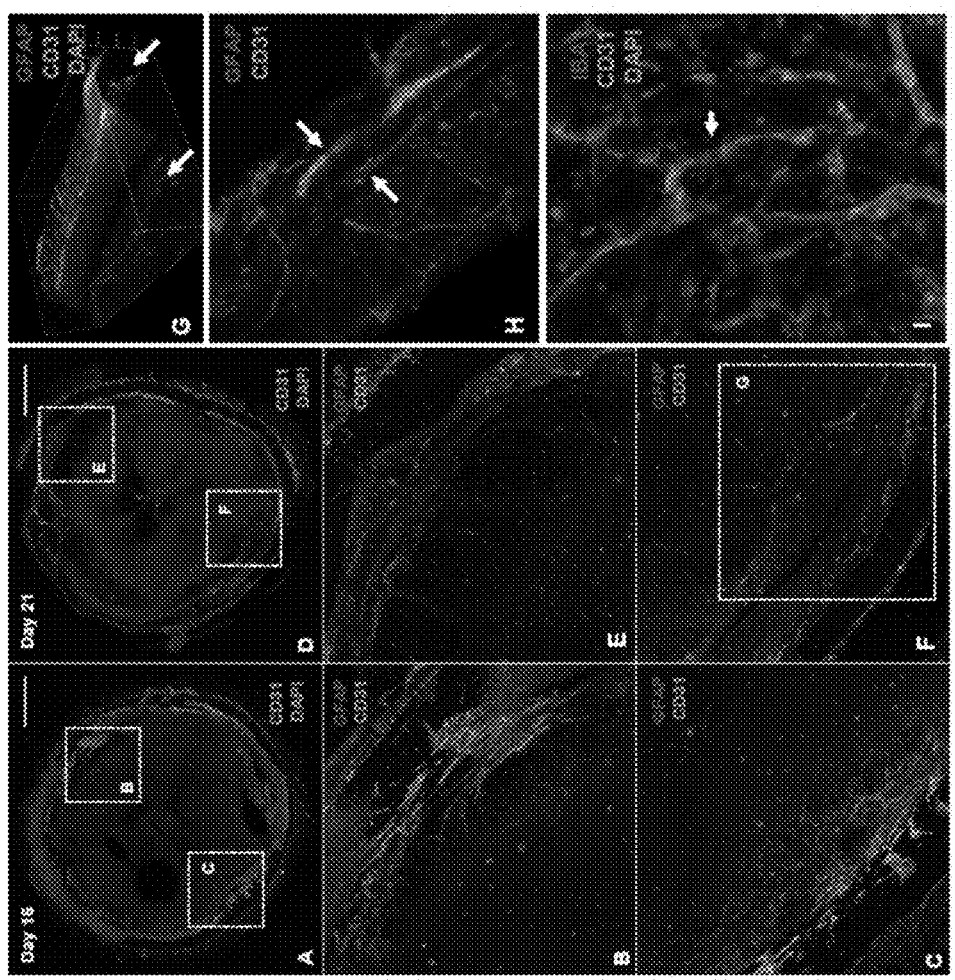
FIGS. 7A-7J present images demonstrating that three-dimensional (3D) neuronal constructs form interconnected vasculature and induce microglia differentiation. Maximum intensity Z-projection immunofluorescence images illustrating vascular networks and microglia within neuronal constructs at (A-C) Day 16 and (D-H) Day 21. Vascularization at day 16 for (A) a full neuronal tissue construct illustrating endothelial cells (CD31, green) and nuclei (DAPI, blue) and (B, C) zoomed images illustrating endothelial cells (CD31, green), glial cells (GFAP, red) within the boxed regions shown in (A). Vascularization at day 21 for (D) a full neuronal tissue construct illustrating endothelial cells (CD31, green) and nuclei (DAPI, blue) and (E, F) zoomed images illustrating endothelial cells (CD31, green), glial cells (GFAP, red) within the boxed regions shown in (D). (G) A reconstructed z-stack (boxed region in F) illustrating capillary tubule formation in distinct layers of the neuronal constructs (arrows). (H) Glial cells (GFAP, red) form connections to capillary-like tubules (CD31, green) through apparent endfeet (arrows). (I) Microglia (IBA1, red) adopt ramified morphologies and incorporate into vascular networks (CD31, green) (arrow). (J) Microglia (IBA1, white), glial cells (GFAP, red), and endothelial cells (CD31, green) for consecutive z-slices to illustrate depth. Endothelial cells and mesenchymal cells were added to the neuronal constructs at day 9 and microglia were added at day 13. Scale bars: (A,D) 1000 μm; (B,C,E,F) Image size 1000×1000 μm.
Figures 8A, 8B, 8C, 8D:
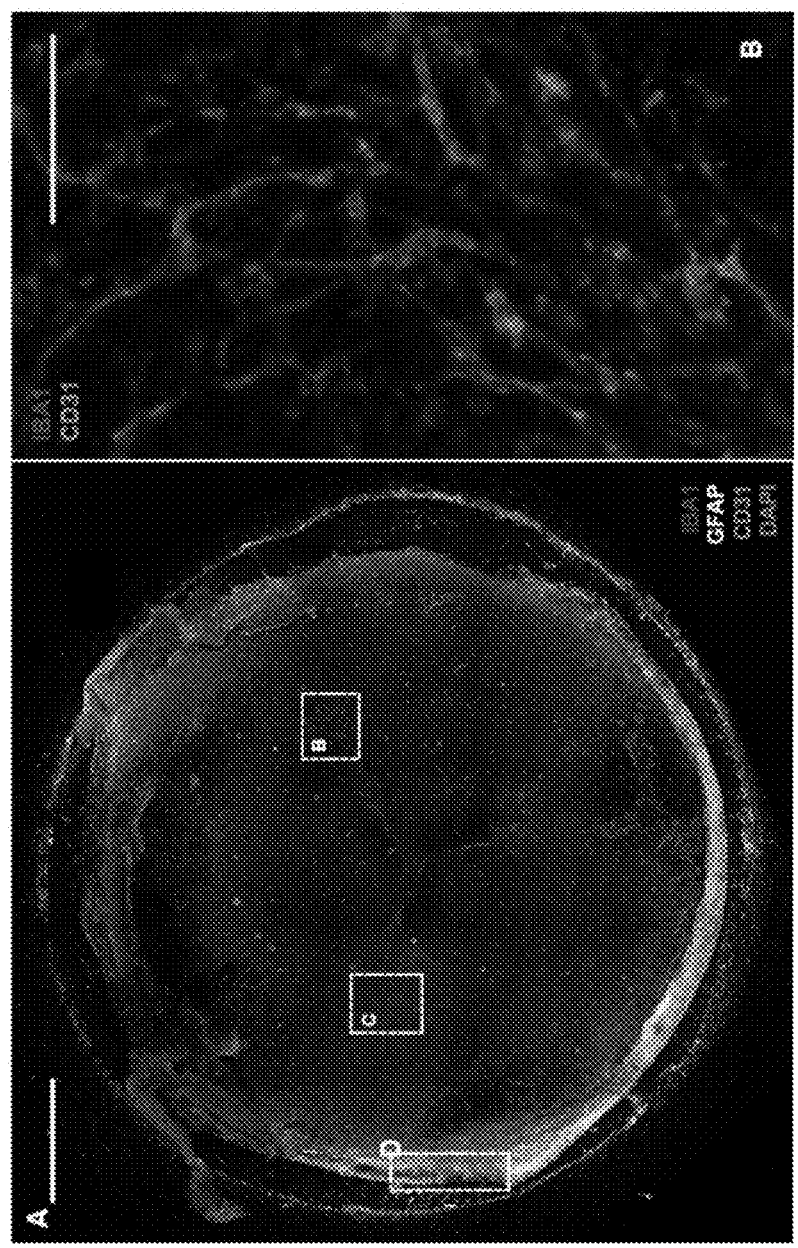
FIGS. 8A-8D present images of microglia differentiation induced in three-dimensional constructs. (A-D) Microglia (IBA1, red), glial cells (GFAP, white), and endothelial cells (CD31, green). (A) Full neuronal construct. (B) Reconstructed Z-stack illustrating boxed region in (A). (C, D) Maximum projection Z-stacks for boxed regions in (A) to show upper and lower regions of the neuronal construct. Scale bars: (A, B) 1000 µm, (C) (D).

The present invention is based at least in part on the Inventors' discovery of methods for directing the differentiation of human pluripotent stem cells into microglia, a type of glial cell that are the resident macrophages of the central nervous system (CNS). Microglia act as the first and main form of active immune defense in the CNS. Microglia have been found to be the primary source of brain cytokines and have been implicated in neuronal pathologies associated with stroke, chronic neuroinflammation (e.g., Alzheimer's disease), and traumatic brain injury. For review, see Giulian et al., *J. Neurosci.* 15(11):7712-7726 (1995). Long thought to be derived from bone marrow, microglia have recently been shown to be derived from primitive macrophages in the earliest wave of hematopoiesis in the yolk sac. See Ginhoux et al., *Science* 330(6005):841-5 (2010). Prior to the Inventors' discoveries, there were no known protocols for deriving this cell type from human pluripotent stem cells. Moreover, obtaining and maintaining primary microglia cultures is difficult. The Inventors discovered a primitive, macrophage-like cell type of the hematopoietic lineage that has the capability to develop ramified human microglia when added to neural tissues. Accordingly, the present invention provides methods of efficiently and reproducibly producing and expanding human microglia suitable for predictive analysis of candidate neurotoxic agents and other human tissue modelling applications. The present invention provides the first opportunity to study these cells in the proper environment in an in vitro human model.

Methods

In exemplary embodiments, the methods provided herein comprise differentiating human pluripotent stem cells under conditions that promote differentiation of the pluripotent stem cells into hematopoietic precursor cells, primitive macrophages, and microglia. Generally, these cell types are identified by their surface phenotype, by the ability to respond to growth factors, and being able to differentiate in vivo or in vitro into particular cell lineages. As used herein, the terms "hematopoietic precursor cells (HPCs)" and "hematopoietic progenitors" refer to immature progenitor cells of the hematopoietic lineage. HPCs are characterized by surface expression of CD45 and, in some cases, CD34, and a capacity to differentiate into myeloid progenitors. HPCs are also known as hematovascular mesoderm progenitors. As used herein, "myeloid progenitors" are cells capable of differentiating into cell types of the myeloid lineages. As used herein, the term "primitive macrophages" refers to myeloid cells derived from HPCs and characterized by CD45 expression and low or no expression of CD34. Primitive macrophages are also characterized by expression of cell surface markers CD14 and CD11b, but show variable expression of CD68 (a marker of more mature macrophages) and do not express Iba-1 at a level that is detectable by, for example, flow cytometry. Human pluripotent stem cell-derived primitive macrophages obtained according to a method provided herein can be cultured under particular culture conditions and contacted to a synthetic or engineered construct comprising neurons and glia for maturation into ramified microglia.

In a first aspect, a method of obtaining HPCs comprises culturing human pluripotent stem cells in a chemically defined culture medium under normoxic conditions (i.e., where oxygen is provided at or about standard atmospheric levels) for about 24 hours. Preferably, the pluripotent stem cells are cultured in a chemically-defined basal culture medium formulation comprising the defined components of culture medium "DF3 S" as set forth in Chen et al., *Nature Methods* 8:424-429 (2011), which is incorporated by reference herein as if set forth in its entirety. As used herein, the terms "E7 culture medium" and "E7" are used interchangeably and refer to a chemically defined culture medium comprising or consisting essentially of DF3S supplemented to further comprise insulin (20 µg/mL), transferrin (10.67 ng/mL) and human Fibroblast Growth Factor 2 (FGF2) (100 ng/mL).

As used herein, the terms "E8 culture medium" and "E8" are used interchangeably and refer to a chemically defined culture medium comprising or consisting essentially of DF3S supplemented by the addition of insulin, transferrin, human FGF2 (100 ng/mL), and human TGFβ1 (Transforming Growth Factor Beta 1). As used herein, "E8 medium" refers to the chemically defined culture medium having the following defined components: DMEM/F12, L-ascorbic acid-2-phosphate magnesium (64 mg/L), sodium selenium (14 µg/L), and NaHCO$_3$ (543 mg/L), transferrin (10.7 mg/L), insulin (20 mg/L), FGF2 (100 m/L) and TGFβ1 (2 µg/L). Normoxic conditions are oxygen conditions of about 15% to about 20% oxygen (e.g., about 15%, 16%, 17%, 18%, 19%, 20% O$_2$). In some cases, the chemically defined culture medium additionally comprises a Rho kinase inhibitor (ROCK inhibitor). ROCK inhibitors can be selected from the group consisting of Y-27632, Blebbistatin (a selective and high-affinity small molecule inhibitor of myosin heavy chain ATPase), and HA1077 (fasudil). For example, a chemically defined culture medium appropriate for use according to the methods described herein can be E8 medium supplemented with ROCK inhibitor Y-27632.

According to this differentiation protocol, pluripotent stem cells are cultured through the HPC differentiation step on a substrate that promotes cell adhesion. In exemplary embodiments, the substrate comprises Tenascin-C ("TenC"). TenC is expressed by mesenchymal cells underlying hematopoietic clusters in the aorta-gonado-mesonephros region and is required for intraembryonic and postnatal hematopoiesis (Marshall et al., *Dev. Dyn.* 1999; 215:139-147; Nakamura-Ishizu et al., *Blood* 2012, 119:5429-5437; Ohta et al., *Blood.* 1998; 91:4074-4083). Recombinant human TenC is commercially available from EMD Millipore. After differentiation of the pluripotent stem cells into HPCs on a TenC-coated surface, subsequent differentiation steps can take place on one or more of the following surfaces: a non-adherent surface, a substrate comprising TenC, a substrate comprising a recombinant human vitronectin polypeptide or fragment or variant thereof, or a self-coating substrate such as Synthemax® (Corning), or a combination thereof.

For directed differentiation of the hematopoietic progenitor cells into myeloid progenitors, the pluripotent stem cell-derived HPCs are cultured about 3 days to about 5 days in a chemically defined, xeno-free culture medium comprising FGF2, VEGF, thrombopoietin (TPO), stem cell factor (SCF), interleukin-6 (IL-6), and interleukin-3 (IL-3), where the hematopoietic progenitor cells differentiate into myeloid progenitors.

For directed differentiation of the myeloid progenitors in primitive macrophages, the myeloid progenitors are cultured in the presence of a chemically defined culture medium comprising insulin and granulocyte macrophage colony-stimulating factor (GM-CSF), a hematopoietic cytokine, whereby the cultured myeloid progenitors differentiate into a cell population comprising at least 80% $CD45^+/CD11b^+/CD14^+$ primitive macrophages. Recombinant human GM-CSF and related cytokines are commercially available.

In another aspect, a method of directing differentiation of human pluripotent stem cells into HPCs comprises culturing the pluripotent stem cells under hypoxic conditions (i.e., where oxygen is provided at a level lower than atmospheric) for about 40 hours to about 48 hours in a chemically defined culture medium comprising one or more of the following factors: a ROCK inhibitor (e.g., Y-27632), bone morphogenetic protein 4 (BMP4), Activin A, and an inhibitor of glycogen synthase 3 (GSK3). Preferably, the GSK3 inhibitor is selected from CHIR99021 (6-[[2-[[4-(2,4-Dichlorophenyl)-5-(5-methyl-1H-imidazol-2-yl)-2-pyrimidinyl]amino]ethyl]amino]-3-pyridinecarbonitrile), lithium chloride (LiCl), and 6-bromoindirubin-3'-oxime (BIO). Hypoxic conditions are characterized by an oxygen concentration less than about 10%. Preferably, hypoxic conditions are characterized by an oxygen concentration of about 1% to 10%, 1% to 9%, 1% to 8%, 1% to 7%, 1% to 6%, 1% to 5%, 1% to 4%, 1% to 3%, or 1% to 2%. In exemplary embodiments, cells are cultured under hypoxic conditions of about 5% $O_2$ or lower (e.g., about 5%, about 4%, about 3%, about 2%, about 1%). The human pluripotent stem cells can be cultured on any appropriate surface (e.g., two-dimensional or three-dimensional).

According to this differentiation protocol, pluripotent stem cells are cultured through the HPC differentiation step on a substrate comprising vitronectin polypeptides or fragments or variants thereof. In exemplary embodiments, human pluripotent stem cells are cultured on a vitronectin-coated surface for directed differentiation at a cell density between about $2 \times 10^5$ cells per $cm^2$ and about $2.5 \times 10^5$ cells per $cm^2$. After differentiation of the pluripotent stem cells into HPCs, subsequent differentiation steps (as set forth below) can take place on a vitronectin-coated surface, a non-adherent surface, or a TenC-coated surface.

In some cases, the method comprises further culturing the cultured pluripotent stem cells (cultured as described above) under hypoxic conditions in a culture medium comprising a Fibroblast Growth Factor (FGF), a vascular endothelial growth factor (VEGF), and an inhibitor of TGFβ-mediated signaling, where culturing occurs for a length of time sufficient for the cultured pluripotent stem cells to differentiate into hematopoietic precursor cells. In some cases, the VEGF is VEGF-A or an isoform thereof. In some cases, the FGF is FGF2. The inhibitor of TGFβ-mediated signaling can be selected from the group consisting of SB-431542, a selective inhibitor of the activin receptor-like kinase receptors ALK5, ALK4, and ALK7; and A-83-01.

Methods of the present invention further comprise directing differentiation of pluripotent stem cell-derived HPCs into progenitors of the myeloid lineages (i.e., granulocyte, macrophage, erythroid, and megakaryocyte) from pluripotent stem cell-derived hematopoietic precursor cells. In humans, common myeloid progenitors (CMPs), which are progenitor cells committed to the myeloid lineages, express CD34 and IL-3 R alpha (CD123). In exemplary embodiments, a method of obtaining myeloid progenitors comprises culturing pluripotent stem cell-derived hematopoietic precursor cells under normoxic conditions (i.e., atmospheric oxygen levels) in a chemically defined growth medium comprising or consisting essentially of a FGF, a VEGF, thrombopoietin (TPO), and at least one cytokine selected from SCF, IL-6, and IL-3, or a mixture thereof. In some cases, the VEGF is VEGF-A or an isoform thereof. In some cases, the FGF is FGF2.

Preferably, the method further comprises culturing the cultured pluripotent stem cell-derived HPCs under normoxic conditions in a myeloid differentiation culture medium. In exemplary embodiments, a myeloid differentiation culture medium is a chemically defined growth medium comprising one or more hematopoietic cytokines such as granulocyte-macrophage colony stimulating factor (GM-CSF; also known as colony stimulating factor 2 (CSF2)), interleukin-3 (IL-3), or interleukin-5 (IL-5). These cytokines are members of a discrete family of cytokines that regulates the growth, differentiation, migration and effector function activities of many hematopoietic cells and immunocytes (Broughton et al., *Immunological Rev.* 250(1):277-302 (2012)).

Cells are cultured in the myeloid differentiation medium until at least about 80% (e.g., at least 80%, 85%, 90%, 95%, 99%) of the resulting cell population are $CD45^+/CD11b^+/CD14^+$ myeloid progenitor cells that express little, if any, CD34. Generally, myeloid progenitor cells are characterized by their expression of cell surface markers. For several of these markers, the expression will be low or intermediate in level. While it is commonplace to refer to cells as "positive" or "negative" for a particular marker, actual expression levels are a quantitative trait. The number of molecules on the cell surface can vary by several logs, yet still be characterized as "positive." Accordingly, characterization of the level of staining permits subtle distinctions between cell populations. Expression levels can be detected or monitored by flow cytometry, where lasers detect the quantitative levels of fluorochrome (which is proportional to the amount of cell surface antigen bound by the antibodies). Flow cytometry or fluorescence-activated cell sorting (FACS) can be used to separate cell populations based on the intensity of antibody staining, as well as other parameters such as cell size and light scatter. Although the absolute level of staining may differ with a particular fluorochrome and antibody preparation, the data can be normalized to a control.

A loss of or reduction in CD34 expression is indicative of a transition from a hematopoietic stem cell (HSC)-like progenitor cell to a myeloid progenitor cell: a $CD45^+/CD11b^+/CD14^+$ primitive macrophage. Primitive macrophages exhibit variable expression of CD68, which is a biological marker of more mature macrophages, and do not express a detectable level of Iba-1.

In exemplary embodiments, primitive macrophages derived according to the methods described herein are further cultured for a minimum of five days in a macrophage differentiation medium comprising Iscove's Modified Dulbecco's Media (IMDM), interleukin-1 beta (IL-1β), and a hematopoietic growth factor such as macrophage colony-stimulating factor (M-CSF), which is also known as colony stimulating factor 1 (CSF1). In some cases, primitive macrophages are cultured in the presence of macrophage differentiation medium for about 5 days and, preferably, contacted to a three-dimensional (3D) neural tissue construct comprising human neurons and glia, whereby the contacted primitive macrophages mature into ramified ("resting") microglia. For example, primitive macrophages cultured in the presence of macrophage differentiation medium for about 5 days are contacted or introduced to a 3D hydrogel-based neural tissue construct as described in U.S. application Ser. No. 14/986,382 and U.S. application Ser. No. 14/986,363 respectively, which are incorporated herein as if set forth in their entirety.

Any appropriate method can be used to detect expression of biological markers characteristic of cell types described herein. For example, the presence or absence of one or more biological markers can be detected using, for example, RNA sequencing, immunohistochemistry, polymerase chain reaction, qRT-PCR, or other technique that detects or measures gene expression. In exemplary embodiments, a cell population obtained according to a method provided herein is evaluated for expression (or the absence thereof) of biological markers of mature microglia such as Iba-1. Myeloid markers and macrophage associated markers include, for example, CD14, CD16, CSFR-1, CD11b, CD206 (also known as macrophage mannose receptor or MMR), CD68, and CD163. Quantitative methods for evaluating expression of markers at the protein level in cell populations are also known in the art. For example, flow cytometry is used to determine the fraction of cells in a given cell population that express or do not express biological markers of interest. Biological markers for perivascular cells and microglia include antibodies having specificity to CD45, CD68, or HLA-DR complex.

As used herein, "pluripotent stem cells" appropriate for use according to a method of the invention are cells having the capacity to differentiate into cells of all three germ layers. Suitable pluripotent cells for use herein include human embryonic stem cells (hESCs) and human induced pluripotent stem (iPS) cells. As used herein, "embryonic stem cells" or "ESCs" mean a pluripotent cell or population of pluripotent cells derived from an inner cell mass of a blastocyst. See Thomson et al., *Science* 282:1145-1147 (1998). These cells express Oct-4, SSEA-3, SSEA-4, TRA-1-60 and TRA-1-81, and appear as compact colonies having a high nucleus to cytoplasm ratio and prominent nucleolus. ESCs are commercially available from sources such as WiCell Research Institute (Madison, Wis.). As used herein, "induced pluripotent stem cells" or "iPS cells" mean a pluripotent cell or population of pluripotent cells that may vary with respect to their differentiated somatic cell of origin, that may vary with respect to a specific set of potency-determining factors and that may vary with respect to culture conditions used to isolate them, but nonetheless are substantially genetically identical to their respective differentiated somatic cell of origin and display characteristics similar to higher potency cells, such as ESCs, as described herein. See, e.g., Yu et al., *Science* 318:1917-1920 (2007).

Induced pluripotent stem cells exhibit morphological properties (e.g., round shape, large nucleoli and scant cytoplasm) and growth properties (e.g., doubling time of about seventeen to eighteen hours) akin to ESCs. In addition, iPS cells express pluripotent cell-specific markers (e.g., Oct-4, SSEA-3, SSEA-4, Tra-1-60 or Tra-1-81, but not SSEA-1). Induced pluripotent stem cells, however, are not immediately derived from embryos. As used herein, "not immediately derived from embryos" means that the starting cell type for producing iPS cells is a non-pluripotent cell, such as a multipotent cell or terminally differentiated cell, such as somatic cells obtained from a post-natal individual.

Human iPS cells can be used according to a method described herein to obtain primitive macrophages and microglial cells having the genetic complement of a particular human subject. For example, it may be advantageous to obtain microglia that exhibit one or more specific phenotypes associated with or resulting from a particular disease or disorder of the particular mammalian subject. In such cases, iPS cells are obtained by reprogramming a somatic cell of a particular human subject according to methods known in the art. See, for example, Yu et al., *Science* 324(5928):797-801 (2009); Chen et al., *Nat. Methods* 8(5): 424-9 (2011); Ebert et al., *Nature* 457(7227):277-80 (2009); Howden et al., *Proc. Natl. Acad. Sci. U.S.A.* 108(16):6537-42 (2011). Induced pluripotent stem cell-derived microglial cells allow modeling of drug responses in tissue constructs that recapitulate neural or other tissue in an individual having, for example, a particular disease. Even the safest drugs may cause adverse reactions in certain individuals with a specific genetic background or environmental history. Accordingly, human subject specific iPS cell-derived primitive macrophages and microglia are useful to identify genetic factors and epigenetic influences that contribute to variable drug responses.

Subject-specific somatic cells for reprogramming into induced pluripotent stem cells can be obtained or isolated from a target tissue of interest by biopsy or other tissue sampling methods. In some cases, subject-specific cells are manipulated in vitro prior to use in a three-dimensional hydrogel-based tissue construct of the invention. For example, subject-specific cells can be expanded, differentiated, genetically modified, contacted to polypeptides, nucleic acids, or other factors, cryo-preserved, or otherwise modified prior to introduction to a three-dimensional tissue construct.

In exemplary embodiments, human pluripotent stem cells are cultured in a chemically-defined basal culture medium formulation comprising the defined components of culture medium "DF3S" as set forth in Chen et al., *Nature Methods* 8:424-429 (2011), which is incorporated by reference herein as if set forth in its entirety. DF3S medium: DMEM/F12, L-ascorbic acid-2-phosphate magnesium (64 mg/L), sodium selenium (14 µg/L), and $NaHCO_3$ (543 mg/L). Preferably, human pluripotent stem cells (e.g., human ESCs or iPS cells) are cultured in the absence of a feeder layer (e.g., a fibroblast layer), a conditioned medium, or a culture medium comprising poorly defined or undefined components. As used herein, the terms "chemically defined medium" and "chemically defined cultured medium" also refer to a culture medium containing formulations of fully disclosed or identifiable ingredients, the precise quantities of which are known or identifiable and can be controlled individually. As such, a culture medium is not chemically defined if (1) the chemical and structural identity of all medium ingredients is not known, (2) the medium contains unknown quantities of any ingredients, or (3) both. Standardizing culture conditions by using a chemically defined culture medium minimizes the potential for lot-to-lot or batch-to-batch variations in materials to which the cells are exposed during cell culture. Accordingly, the effects of various differentiation factors are more predictable when added to cells and tissues cultured under chemically defined conditions. As used herein, the term "serum-free" refers to cell culture materials that are free of serum obtained from animal (e.g., fetal bovine) blood. In general, culturing cells or tissues in the absence of animal-derived materials (i.e., under xenogen-free conditions) reduces or eliminates the potential for cross-species viral or prion transmission.

In a further aspect, provided herein is a method of screening a compound for toxicity. In exemplary embodiments, the method comprises exposing a test compound to a composition comprising human microglial cells and assaying for a toxic effect of the compound on one or more aspects of human microglial growth or development. Preferably, the composition is obtained by contacting human pluripotent stem cell-derived primitive macrophages to a chemically defined, xenogen-free three-dimensional (3D) tissue construct that includes stratified layers of human neurons and glia. Upon addition of primitive macrophages to such a 3D composition, the primitive macrophages differentiate to form a composition comprising human microglial cells.

Unless defined otherwise, all technical and scientific terms used herein have the same meaning as commonly understood by one of ordinary skill in the art to which the invention belongs. Although any methods and materials similar to or equivalent to those described herein can be used in the practice or testing of the present invention, the preferred methods and materials are described herein.

As used herein, "a medium consisting essentially of" means a medium that contains the specified ingredients and those that do not materially affect its basic characteristics.

As used herein, "effective amount" means an amount of an agent sufficient to evoke a specified cellular effect according to the present invention.

As used herein, "about" means within 5% of a stated concentration range, density, temperature, or time frame.

The invention will be more fully understood upon consideration of the following non-limiting Examples. It is specifically contemplated that the methods disclosed are suited for pluripotent stem cells generally. All papers and patents disclosed herein are hereby incorporated by reference as if set forth in their entirety.

EXAMPLES

Example 1

Protocol for Directed Differentiation of hESCs into Hematopoietic Precursor Cells The first stage of differentiation requires the derivation of hematopoietic precursor cells (HPCs) from human pluripotent stem cells. The following protocol was developed and validated for obtaining hemogenic endothelium that ultimately gives rise to HPCs. Tenascin C (TenC), an extracellular matrix protein associated with HSC niches, strongly promotes HE and definitive hematopoiesis in this system.

Microglia/macrophage precursors were produced using feeder-free, chemically defined conditions by modifying a previous protocol for differentiating H1 ES cells down mesendoderm and hemogenic endothelium lineages (see Slukvin 2006; Vodyanik et al., Blood (2006) 108:2095-2105). 6-well plates were first coated with 40 µg Tenascin C overnight 4° C. Tenascin C plates were rinsed with PBS, and then seeded with singularized H1 ES cells at a density of 62,500 cells/cm² in E8 medium+10 µM ROCK inhibitor Y-27632. Directed differentiation of the human pluripotent stem cells occurs following culture of the cells in E8 medium+ROCK inhibitor for about 24 hours under normoxic conditions.

E8 Medium: DMEM/F12, L-ascorbic acid-2-phosphate magnesium (64 mg/L), sodium selenium (14 µg/L), and NaHCO₃ (543 mg/L), transferrin (10.7 mg/L), insulin (20 mg/L), FGF2 (100 µg/L) and TGFβ1 (2 µg/L).

Example 2

Alternative Protocol for Directed Differentiation of hESCs into Hematopoietic Precursor Cells and Primitive Macrophages Provided below is an alternative protocol for obtaining HPCs and primitive macrophages from human pluripotent stem cells.

TABLE 1

Differentiation Base Medium

| | Add: | Final Concentration |
|---|---|---|
| Defined component: | | |
| Iscove's Modified Dulbecco's Media (IMDM) + F12 | 500 mL | 1X |
| L-ascorbic acid 2-phosphate Mg2+ salt | 32 mg | |
| Monothioglycerol | 20 uL | |
| Sodium selenite | 6 µL | 0.7 mg/mL |
| Polyvinyl alcohol | | 20 mg/L |
| GlutaMAX ™ 100X supplement (Gibco ®) | 5 mL | |
| Non-Essential Amino Acids Solution (NEAA) (100X) (Gibco ®) | 5 mL | |
| Chemically Defined Lipid Concentrate (CDLC) 100X (Gibco ®) | 5 mL | |
| Base Cytokines | | |
| Insulin | | 10 mg/mL |
| Holo-Transferrin | | 10.6 mg/mL |

TABLE 2

Differentiation Medium 1 (DM1)

| Defined component: (Cytokines 12 mL) | Add: | Final Concentration: |
|---|---|---|
| Base media | 12 mL | 1X |
| FGF2 (100 µg/mL) | 6 µL | 50 ng/mL |
| BMP4 (100 µg/mL) | 6 µL | 50 ng/mL |
| Activin A (10 µg/mL) | 15 µL | 12.5 ng/mL |
| LiCl (2M) | 12 µL | 2 mM |

TABLE 3

Differentiation Medium 2 (DM2)

| Defined component: (Cytokines 12 mL) | Add: | Final Concentration: |
|---|---|---|
| Base media | 12 mL | 1X |
| FGF2 (100 µg/mL) | 6 µL | 50 ng/mL |
| VEGF (100 µg/mL) | 6 µL | 50 ng/mL |
| SB-431542 | | 10 µM |

TABLE 4

Differentiation Medium 3 (DM3)

| Defined component: | Add: | Final Concentration: |
|---|---|---|
| Base media | 12 mL | 1X |
| FGF2 (100 µg/mL) | 6 µL | 50 ng/mL |
| VEGF (100 µg/mL) | 6 µL | 50 ng/mL |
| TPO (100 µg/mL) | 6 µL | 50 ng/mL |

TABLE 4-continued

Differentiation Medium 3 (DM3)

| Defined component: | Add: | Final Concentration: |
|---|---|---|
| SCF (100 µg/mL) | 6 µL | 50 ng/mL |
| IL-6 (100 µg/mL) | 6 µL | 50 ng/mL |
| IL-3 (10 µg/mL) | 12 µL | 10 ng/mL |

TABLE 5

Differentiation Medium 4 (DM4)

| Defined component: | Add: | Final Concentration: |
|---|---|---|
| Base media | 12 mL | 1X |
| GM-CSF | | 200 ng/mL |

TABLE 6

Differentiation Medium 5 (DM5)

| Defined component: | Final Concentration: |
|---|---|
| Iscove's Modified Dulbecco's Media (IMDM) | 1X |
| Heat-inactivated Fetal Bovine Serum (FBS) | 10% |
| IL-1β | 10 ng/mL |
| M-CSF | 20 ng/mL |

Initiate Early Mesoderm Differentiation: Twenty four hours after plating H1 ES cells, E8 media was aspirated and replaced with DM1+1 µM Y-27632. Cells were then cultured under hypoxic conditions (5% $O_2$) for two days (do not expose cells to normoxia) on vitronectin-coated plates. During the two days of culture, cells will detach and reattach. Care is taken to avoid disturbing the culture, as cells tend to aggregate in the middle of the plate and affect differentiation efficiency.

HPC Differentiation and Expansion: On day 2, cultures were checked for surviving cell clumps that have not fully reattached. If cells are still floating, use a 10 ml pipet to pull media off plate, centrifuge floating cells and cell clumps @ 300×g to form a pellet, aspirate DM1 and resuspend in DM2, plate cells back into same plate, and continue culture in a hypoxic incubator. If only debris is present, aspirate DM1 and add DM2 slowly as to not disrupt the adherent cells, continue culture in a hypoxic incubator.

On day 4, DM2 medium was aspirated and replaced with DM3 medium. Culture was continued in a normoxic incubator. On day 6 of culture (2 days after adding DM3 media), additional DM3 media was added without aspirating media already present. Culture was continued in a normoxic incubator. Cells were expanded for an additional 3-5 days in DM3 (or for a longer time if cells are not fully adherent after hematovascular differentiation). If media color indicates a significant drop in pH, half of the media volume was removed and placed in a low-attachment dish. An additional volume of DM3 was added to both culture plates. After 3-5 days, spent media containing floating HPCs was collected and centrifuged @300×g to pellet. The resulting cells are hematopoietic precursor cells (also known as hematopoietic progenitors).

Myeloid Progenitor Differentiation: HPCs were cultured in myeloid progenitor medium DM4, adding $1×10^6$ cells/ml to a low attachment culture dish (at this point, cells can be grown on a 10 cm dish) under normoxic conditions to direct differentiation of the HPCs into myeloid progenitors. The myeloid progenitors were expanded for 2-5 days in DM4 medium (at least 2 days required for proper transition to macrophages), adding media if pH significantly drops (half/half mixture; do not transfer cells). Up to $2×10^7$ myeloid progenitors were obtained per 10 cm dish. During expansion in DM4 medium (2-5 days), floating cells were collected for an optional sorting step to identify $CD34^+$ and $CD45^+$ cells.

Microglia/Macrophage Precursor Differentiation: After 2-5 days of myeloid progenitor expansion, $5×10^5$ floating cells were added to macrophage differentiation medium DM5 in a 10 cm treated tissue culture dish. Cells were cultured for 3 days and then an equivalent volume of DM5 medium (without aspiration) was added. After 5 days (meaning, following 2 additional days in DM5), ~50-70% of cells will have attached. When cells reach ~70-80% confluence (adherent cells), the remaining floating cells were transferred to a new 10 cm dish to promote adhesion. FACS was performed to confirm that the resulting cells are >80% $CD11b^+$, $CD45^+$, and $CD14^+$. See FIGS. 4A-6D. Floating cells are $CD14^{Low/Negative}$ but will continue to mature. On days 5-10, cells begin to attach. These cells (as well as some floating cells) should be $CD11b^+$ and $CD14^+$ (~60-90%). Culture in DM5 medium was continued.

Identification of Cell Types During Directed Differentiation: HPCs were identified based on expression of CD45 (greater than 75%) with a proportion of cells co-expressing CD34. Myeloid progenitors were derived and expanded from this cell population. Cells expressing CD45 (greater than 85%) with little or no CD34 expression, were identified as primitive macrophages. The primitive macrophages also expressed cell surface markers CD14 and CD11b, but showed variable expression of the more mature microglial marker CD68 and did not express Iba-1 at a detectable level as assayed using flow cytometry. See FIGS. 4A-6D. Primitive macrophages were matured for a minimum of five days in a maturation culture medium and were then added to neural tissues to complete the maturation to ramified (mature, resting) microglia.

Assaying for Phagocytosis by Microglia/Macrophage Precursors: Aliquots of zymosan A *S. cerevisiae* BioParticles® (Texas Red® conjugate; Life Technologies) were prepared in PBS. Approximately $5×10^6$ particles in 500 µL PBS were added to each well of a E-well plate containing ~400-500K microglia/macrophage precursors in DM5 media. Phagocytosis was imaged over a 24 hour time period (images captured every 10 min.) using a Nikon Biostation® CT.

Example 3

Characterizing Human Pluripotent Stem Cell-Derived Primitive Macrophages

To demonstrate that human primitive macrophages obtained according to the methods provided herein are structurally and functionally comparable to primary cultures, fluorescently tagged, inactivated yeast particles were added to in vitro cultures to induce phagocytosis. Primitive macrophages completely cleared the cell culture medium of tagged yeast particles within 24 hours of induction. Human embryonic stem cells, which served as a control, did not phagocytize the yeast particles.

To demonstrate that the primitive macrophage cell populations did not comprise microglia, the cells were fixed and stained with a fluorescently tagged antibody specific to Iba-1, a hallmark microglial transcription factor. No Iba-I⁺ cells were observed, indicating that none of the pluripotent stem cell-derived cells had differentiated into microglia.

During the formation of the human cerebral cortex, Iba1+ microglia begin to populate the cortical primordial plexiform layer, or preplate (a transient structure comprising the marginal zone and the subplate that arises during cortical development), as early as 5.5 gestational weeks (GW), but they only minimally interact with blood vessels that have penetrated the human cortex before about 9 GW. To mimic the in vivo recruitment of blood vessels and microglia after the initial formation of the neural tube and the developmental timing when Iba1+ microglia begin to interact with capillaries of the cortex, primitive macrophages were added to a pre-formed hydrogel neural tissue construct complete with embedded vasculature as described in U.S. application Ser. No. 14/986,363, which is incorporated herein as if set forth in its entirety. Primitive macrophages were added to hydrogel neural tissue constructs after initial vascular network organization and after neural progenitor cells had self-assembled into multilayered structures with radially organized neural and glial populations reminiscent of the early neuroepithelium. By day 21 of differentiation on neural tissue constructs, the constructs contained an extensive neural network, cells exhibiting neural and glial phenotypes, interconnected capillary networks, and microglia-like cells. RNA-Seq was used to quantitatively assess sample uniformity by comparing differential gene expression for replicate neural constructs after 14 and 21 days of differentiation on hydrogels. In addition, Iba-I protein expression was detected by fluorescent antibody staining. Replicate samples were characterized by Spearman's correlation coefficients $(\rho) \geq 0.99$ to at least 21 days of differentiation. See Table 7 and FIGS. 3A-3D. RNA sequencing (RNA-seq) revealed an increase in expression of CD68, a microglial cell marker. RNA-seq also identified several characteristic microglia genes that were detectable only when primitive macrophages/microglia precursor cells were incorporated into the neural constructs, such as CD11B (ITGAM), TREM2, and IBA1 (AIF1). Iba1+ cells were distributed throughout the neural constructs by day 21 (FIGS. 2A-2G), and adopted ramified morphologies, which is a distinguishing feature for microglia in the resting state. Iba1+ cells associated with endothelial tubules (FIGS. 2A-2G, 3A-3D, 7A-7J, and 8A-8D), which has been observed during human development and suggests a possible role for microglia in guiding vascular organization within the neural constructs. Therefore, human ES cell-derived primitive macrophages exhibit several properties consistent with a microglia-like phenotype observed within the neural constructs. These data demonstrate that three-dimensional multilayered neural tissue-like constructs can be produced with remarkable uniformity when ES cell-derived precursor cells are cultured on bioactive hydrogels.

Figure 9:
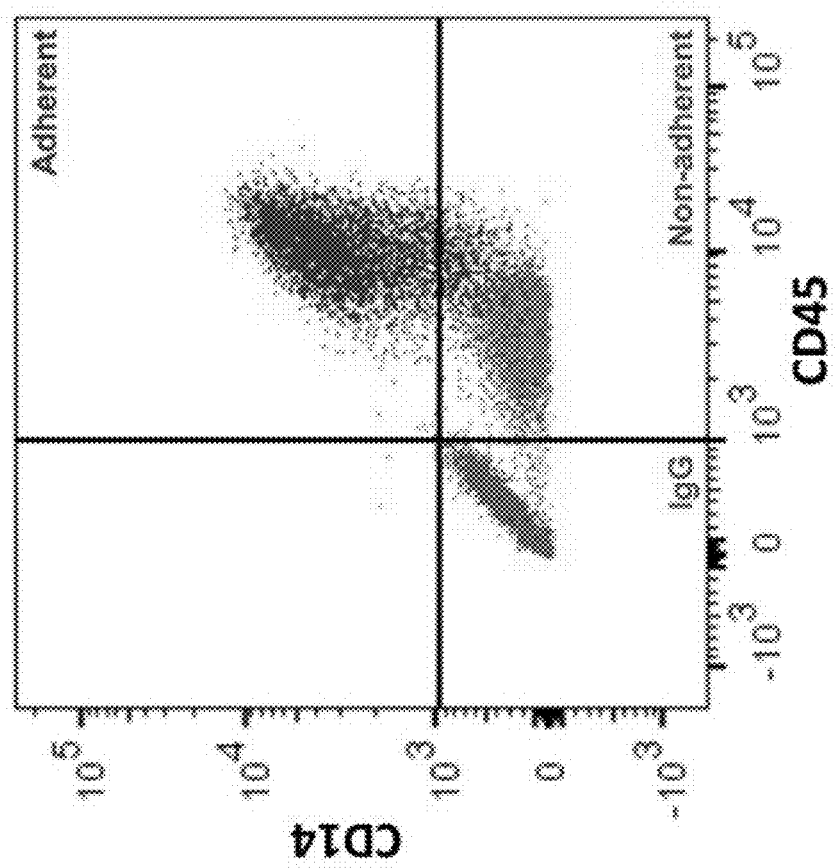
FIG. 9 is a FACS plot demonstrating microglia and macrophage precursor (MG) differentiation. Both adherent and nonadherent populations will be CD45$^+$ (right-hand quadrants), but non-adherent cells will be CD14$^{Low/Negative}$ (lower left quadrant) and adherent cells will be CD11b$^+$/CD14$^+$ (upper right quadrant; "MG").

FIG. 9 presents FACS data for Microglia and macrophage precursor (MG) differentiation. Both adherent and nonadherent populations are CD45+, but non-adherent cells are CD14$^{Low/Negative}$ and adherent cells are CD11b+CD14+. On days 5-10, non-adherent cells began to attach and differentiate into CD11b+ and CD14+ cells.

TABLE 7

Gene Expression in Neural Constructs

| Genes | Average | | Standard Deviation | |
| --- | --- | --- | --- | --- |
| | Day 16 | Day 21 | Day 16 | Day 21 |
| AIF1/IBA1 | 12.1 | 15.6 | 3.3 | 8.8 |
| ITGAM/CD | 2.3 | 1.2 | 0.6 | 1.2 |
| PTPRC | 4.1 | 3.6 | 0.9 | 3.3 |
| CX3CR1 | 3.8 | 3.7 | 0.8 | 4.6 |
| CD68 | 17.3 | 23.8 | 4.0 | 18.9 |
| CD14 | 1.8 | 3.0 | 1.6 | 1.4 |

Normalized expression (TPM; N = 4)

Materials and Methods—Neural Tissue Constructs Comprising Pluripotent Stem Cell-Derived Microglia/Macrophage Precursors Hydrogel Polymerization: Polyethylene glycol (PEG) hydrogels were formed using thiol-ene photopolymerization chemistry, with modifications from previously a published protocol (Fairbanks 2009). Stock solutions of 8-arm PEG-norbornene (20000 MW, JenKem USA, 8ARM (TP)-NB-20K) were prepared at a final concentration of 300 mg/mL by dissolving 300 mg of solid/0.8 mL PBS to account for volume occupied by 8-arm PEG-norbornene solid, sterile filtered through a 0.2 µm nylon syringe filter (Fisher), and stored as frozen aliquots. Matrix metalloproteinase (MMP)-degradable PEG hydrogels were formed using an amino acid sequence modified from a native collagen sequence (Nagase 1996) (KCGPQG~IWGQCK (SEQ ID NO:1); Active sequence in bold, cleave site=(~); Genscript, >90% purity, C-terminus amidated), with cysteines on each end to crosslink 8-arm PEG-norbornene molecules. Cell adhesion was promoted by incorporating CRGDS peptide (SEQ ID NO:2) (2 mM final monomer solution concentration; Genscript, >90% purity, C-terminus amidated), an amino acid sequence derived from fibronectin (Pierschbacher 1984). Stock MMP-peptide (~75 mM peptide/150 mM SH) and CRGDS peptide (~100 mM) solutions were prepared and sterile filtered through a 0.22 µm low protein binding polyvinylidene difluoride (PVDF) syringe filter (Millex) and the final concentration was verified after filtration using an Elman's assay (Thermo Scientific; modification of Manufacturier's protocol: PBS used to dissolve all reagents).

The final monomer formulation for PEG hydrogels was 40 mg/mL 8-arm PEG-NB, 4.8 mM MMP-peptide cross-linker (9.6 mM cysteines, 60% molar ratio relative to norbornene arms), 2 mM CRGDS (SEQ ID NO:2), and 0.05% (wt/wt) Irgacure® 2959 photoinitiator (BASF Schweiz AG, Basel, Switzerland). Hydrogels were formed by pipetting 30 µL monomer into 24-well BD Transwell inserts (1 µm pores, Fisher; Quality control experiments) or 40 µL into Corning HTS Transwell-24 well permeable support (0.4 µm pores, Sigma Aldrich; Toxicity experiments). After pipetting, any gaps between the PEG monomer solution and the edge of the insert (due to surface tension) were removed by tilting the insert plate and gently tapping until the solution uniformly covered the bottom of the transwell insert membrane. Transwell plates containing inserts and monomer solutions were placed on the top shelf of a UVP XX-15 lamp stand (Fisher) and exposed to ~365 nm centered UV light (UVP XX-15L lamp, Fisher) for 2.5 minutes. After polymerization, hydrogels were incubated in DF3S medium overnight to allow swelling and equilibration (5% $CO_2$, 37° C.).

Seeding H1 ES Cell-Derived Neural Progenitor Cells (NPCs) on PEG Hydrogels: Cryopreserved NPCs were thawed and expanded on 6-well plates coated with Matrigel® (BD Biosciences, 0.5 mg per plate for at least 1 hour) and cultured in neural expansion medium. One vial of frozen NPCs (~1.2×10$^7$ cells) was thawed and plated in 3 wells of a Matrigel® coated 6-well plate (2 vials were thawed in one Matrigel® coated 10 cm dish), cultured for 2-3 days (depending on initial confluence) and passaged 1:3 using Accutase™. NPCs were passaged 1:3 after 2 days of additional culture, expanded for 2-3 more days and used for experiments.

NPCs were removed from the plate using 1 mL Accutase/well, from which an aliquot was removed for counting. After adding the appropriate volume of cell suspension to a conical vial, NPCs were pelleted at 0.2 G for 4 minutes. NPCs were resuspended and seeded in neural expansion medium at a density of 100,000 cells/24-well insert. NPCs were allowed to attach overnight, and then neural expansion medium was exchanged on Day 1 and every 2 days for the remainder of the experiment. For each medium exchange, all medium under the insert was aspirated, while approximately ¾ of the medium was removed from the top by sliding the pipette tip down the side of the well to avoid damaging the developing neural tissue constructs.

Differentiation and Growth on PEG Hydrogels of H1 ES Cell-Derived Endothelial Cells (ECs), Mesenchymal Stem Cells (MSCs), and Microglia/Macrophage Precursors (MG): Endothelial cells were expanded from cryopreserved stocks on fibronectin-coated plates (Life Technologies, 100 µg per plate) using E7BV media, with one vial (~1×10$^6$ cells) per 6 wells of a 6-well plate or a single 10 cm dish. ECs were split 1:3 after 2 days using Accutase, cultured for an additional 3 days, and then used for experiments.

E8BA medium: E8 supplemented with BMP4 (5 µg/L) and Activin A (25 µg/L). E7V medium: E8 minus TGFβ1, supplemented with VEGF-A (50 µg/L). E7BVi medium: E7V supplemented with BMP4 (50 µg/L) and SB431542 (5 µM, TGFβ inhibitor) (Inman 2002). E7BV medium: E7V supplemented with BMP4 (50 µg/L).

At day 9, endothelial cells (ECs) and MSCs were seeded on top of the differentiating NPC layer at a total density of 100,000 cells/well, with a 5:1 ratio of ECs:MSCs (83.3K: 16.7K) (FIGS. 1A-1B). Both ECs and MSCs were harvested using Accutase and counted before centrifugation. Cells were counted and mixed in the appropriate ratio, centrifuged, and resuspended for seeding. Neural expansion medium was exchanged on day 11 (2 days after seeding ECs and MSCs). At day 13, microglia/macrophage precursors were harvested and seeded at a density of 100,000 cells/insert (FIGS. 1A-1B). Neural expansion medium was exchanged on day 14, and then every other day until samples were collected for RNA, sorting, or immunofluorescence imaging.

Human ES Cell Differentiation into Microglia/Macrophage Precursors (MG):

Microglia/macrophage precursors were produced using feeder-free conditions by modifying a previous protocol for differentiating H1 ES cells down mesendoderm and hemogenic endothelium lineages (see Uenishi et al. (2014) *Stem Cell Rep* 3(6):1073-1084). E-well plates were first coated with 40 µg Tenascin C overnight at 4° C. Tenascin C plates were rinsed with PBS, and then seeded with singularized H1 ES cells at a density of 62,500 cells/cm$^2$ in E8 medium+10 µM Y-27632 (ROCK inhibitor, R&D Systems). Cells were cultured for 24 hours under normoxic conditions.

Initiate Early Mesoderm Differentiation. 24 hours after plating H1 ES cells, E8 media was aspirated and replaced with DM1+1 µM Y-27632. Cells were then cultured under hypoxic conditions (5% $O_2$) for two days (do not expose cells to normoxia). During the two days of culture, cells detach and reattach. It is important that the culture is not disturbed, as cells will aggregate in the middle of the plate, affecting differentiation efficiency.

Continue Hematovascular Mesoderm Differentiation. On day two, the culture was checked for surviving cell clumps that had not fully reattached. If non-adherent cells were present, a 10 mL pipette tip was used to gently pull media off plate, and the non-adherent cells and cell clumps were centrifuged at 300×g for five minutes to form a pellet. DM1 was aspirated from the pellet, and the cells were resuspended in DM2. Cells were gently plated back into same plate, and culture was continued in a hypoxic incubator. If only debris was present, DM1 was aspirated and DM2 was added slowly as to not disrupt the adherent cells. Culture was continued in a hypoxic incubator.

Differentiate and Expand Hemogenic Endothelial Cells into Hematopoietic Progenitor Cells (HPCs). On day 4, DM2 medium was aspirated and replaced with DM3 medium. Culture was continued under normoxic conditions. On day 6 of culture (two days after adding DM3 media), additional DM3 media was added without aspirating media already present. Culture was continued in a normoxic incubator. Cell cultures were expanded for an additional 3-5 days in DM3 (longer time is required when cells not fully adherent after hematovascular differentiation). If media color indicated a significant pH drop, half of the media volume was removed from the plate and placed into a low attachment dish. An additional volume of DM3 (1:1 mix of old and fresh media) was added to both culture plates. After 3-5 days, spent media containing non-adherent HPCs was collected and centrifuged at 300×g for about five minutes to pellet.

Myeloid Progenitor (MP) Differentiation. Expansion was continued in myeloid progenitor medium DM4, where 1×10$^6$ HPCs/mL were to a low attachment culture dish under normoxic conditions. At this point, the cells could be grown in a 10 cm dish under normoxic conditions. Cells were expanded for 2-5 days in the DM4 medium. At least five days in culture was required for proper transition to macrophages, but no more than five days. DM4 was added if the culture's pH significantly dropped (half/half mixture; do not transfer cells). Up to 2×10$^7$ cells were obtained from a 10 cm dish. During expansion in DM4 medium (2-5 days), non-adherent cells were collected for sorting to identify CD34$^+$ and CD45$^+$ cells.

Microglia/Macrophage Precursor (MG) Differentiation. After 2-5 days of myeloid progenitor expansion, 5×10$^5$ non-adherent cells were added to macrophage differentiation medium DM5 in a 10 cm tissue culture treated dish. Cells were cultured for three days, then an equivalent volume of DM5 media was added without aspiration of the media. After five days (two additional days in DM5), ~50-70% of cells had attached. When cells reached ~70-80% confluence (adherent cells), remaining non-adherent cells were transferred to a new 10 cm dish to promote adhesion. As shown in FIG. 9, both adherent and non-adherent populations are CD45$^+$, but non-adherent cells will be CD14$^{Low/Negative}$ and adherent cells will be CD11b$^+$/CD14$^+$. On days 5-10, non-adherent cells began to attach and differentia into CD11b$^+$ and CD14$^+$ cells. Culture in DM5 medium was continued.

Toxicity Screening Experiments: For toxicity screening experiments, cells were seeded as described above, but with 65,000 cells/well for ECs+MSCs (also 5:1 ratio) and 15,000 cells/well for microglia/macrophage precursors. Neural constructs were treated with non-toxic or toxic compounds starting at day 14, with medium exchanged every 2 days.

Toxic chemicals were chosen based on previous literature support for neurotoxicity (Adams 1993; Cooper 1998; Crofton 2011; Eskes 2003; Grandjean 2014; Lidsky 2003; Radio 2010; Zurich 2002).

For the quality control assays, RNA was collected on days 14 and 21. For the 3D toxicity screening experiments, RNA was collected on days 16 and 21 (permitting 2 days of chemical exposure before collecting at the first time point).

Immunofluorescence Imaging: Blocking buffer: 0.25% Triton X-100 and 1% BSA in PBS; Incubation buffer: 0.05% Triton X-100 and 1% BSA in PBS; Rinse buffer: 0.05% Triton X-100 in PBS.

Primary Antibodies: Rabbit anti-β3-tubulin (1:500; Cell Signaling, mAb #5568S), mouse anti-β3-tubulin (1:500; R&D Systems, MAB1195), rabbit anti-calretinin (1:100-1:200: Abcam, ab137878), rabbit anti-GABA (1:200: Abcam, ab43865), rabbit polyclonal fibrillary acidic protein (GFAP) (1:500; Dako, Z033401-2), goat anti-glial fibrillary acidic protein (GFAP) (1:100-1:200; C-19; sc-6170, Santa Cruz Biotechnology), mouse anti-phospho-vimentin (1:200; S55 [4A4]; Abcam, ab22651), mouse anti-CD31 (1:200; Endothelial Cell, Clone JC70A; DAKO, M082301-2), mouse anti-04 (1:100-1:200; clone 81; Millipore, MAB345), Chicken polyclonal anti-Tbr1 (1:100-1:200; Millipore, AB2261), mouse anti-SOX-2 (Cell Signaling, mAb #4900S), rabbit anti-SOX-2 (Cell Signaling, mAb #3579S), mouse anti-MAP2, (clone AP20; Millipore, MAB3418), mouse anti-Reelin (1:100; clone G10, a.a. 164-496; Millipore, MAB5364), mouse anti-Brn-2 (POU3F2) (1:200; clone 8C4.2; Millipore, MABD51), rabbit anti-Brn-2 (POU3F2) (1:200; Cell Signaling, mAb #12137S), rabbit anti-Ctip2 (Bcl-11b) (1:200; Cell Signaling, mAb #12120S), rabbit anti-VGLUT2 (1:100; Abcam), mouse anti-MAP2 (1:500; clone AP20; Millipore, MAB3418), goat anti-Iba1 (1:100; Abcam, ab5076), rabbit anti-Tyrosine Hydroxylase (Cell Signaling, mAb ##27925), rabbit anti-PDGFR-α (1:100; Santa Cruz Biotechnology, sc-338).

Secondary Antibodies: Alexa Fluor secondary antibodies were used for all experiments (Life Technologies): Donkey anti-goat 568 (A11057) or 647 (A21447); Donkey anti-rabbit 488 (A21206), 568 (A10042), or 647 (A-31573); Donkey anti-mouse 488 (A-21202), 568 (A10037), or 647 (A31571); Goat anti-chicken (A11041).

Immunostaining Full Neural Constructs: All steps for immunostaining were performed within transwell inserts. Neural constructs were fixed for 60 min. using 2% buffered formalin and then rinsed with PBS (or stored at 4° C. until immunostaining). Neural constructs were permeabilized and blocked in blocking buffer (at least 60 min.). For some experiments, blocking buffer was used for all steps until final rinse, with similar results. Primary antibodies were prepared in incubation buffer, added to the neural constructs, and incubated overnight at 4° C. Neural constructs were then rinsed (2× with rinse buffer, at least 60 min./ea.) followed by a third rinse step (blocking buffer, at least 60 min.). Secondary antibodies and 1:1000 DAPI (Sigma) were prepared in incubation buffer, added to the neural constructs, and incubated overnight at 4° C. (or at least 4 hours at room temperature). Neural constructs were rinsed 2×60 min. in rinse buffer, followed by an overnight rinse at 4° C. in incubation buffer. Samples were then stored in PBS until further processing (typically at least 24 hours).

Neural constructs were removed from the transwell insert by cutting the bottom edge of the membrane, separated from the membrane, and mounted in aqua polymount solution (Polysciences, Inc.) on the bottom of a 35 mm glass bottom dish (MatTek). To limit bubble formation in the mounting solution, a thin layer was first added to the glass bottom of the 35 mm dish. The neural construct was usually placed face down into the layer of mounting solution (with some samples placed face up), after which a drop of mounting solution was added to cover the construct. A coverslip was then dropped onto the neural construct in mounting solution and allowed to settle, rotating the dish to ensure uniform coverage of the mounting solution under the coverslip. The coverslip was allowed to settle overnight at 4° C., and sealed around the edges with fingernail sealant. The samples remained stable for imaging for at least 1 month.

Immunostaining Cryopreserved Sections: Neural constructs were fixed in the transwell insert for 60 min. using 2% buffered formalin and rinsed with PBS (overnight at 4° C.). The samples were then rinsed in 15% Sucrose/PBS (at least 24 hours, 4° C.) followed by 30% Sucrose/PBS (at least 24 hours, 4° C.). Neural constructs were removed from the transwell insert by cutting the bottom edge of the membrane, separated from the membrane, and placed face down into cryogel (Tissue-Tek embedding medium), and stored frozen at −80° C. until further processing. Frozen samples were equilibrated to −20° C. and sectioned (20-30 µm sections on glass slides). Glass slides containing sectioned samples were soaked in deionized water for at least 1 hour to remove cryogel. Samples were permeabilized and blocked in blocking buffer for 60 min., rinsed 2×15 min. with rinse buffer, and incubated at room temperature in incubation buffer for at least 60 min. Samples were then treated with primary antibodies in incubation buffer at 4° C. (or at least 4 hours at room temperature). Samples were then rinsed with wash buffer (2×15 min.) and incubation buffer (at least 60 minutes, room temperature). Samples were then treated with secondary antibodies and 1:1000 DAPI (Sigma) in incubation buffer overnight at 4° C. (or at least 2 hours at room temperature). Sectioned samples were mounted in aqua polymount solution (Polysciences, Inc.), a glass coverslip was placed over the top, stored overnight at 4° C., and sealed around the edges with fingernail sealant until imaging.

Image Processing: Confocal immunofluorescence images were collected using a Nikon MR confocal microscope. Images were processed using NIS Elements or ImageJ (Rasband 1997-2012; Schneider 2012). Some z-stacks were aligned using the "Align Current ND Document" (NIS Elements) or the StackReg plugin (ImageJ) before creating maximum projection images.

REFERENCES

1. D. Rice, S. Barone, *Environ. Health Perspect.* 108, 511 (June, 2000).
2. L. Smirnova, H. T. Hogberg, M. Leist, T. Hartung, *ALTEX-Altern. Anim. Exp.* 31, 129 (2014).
3. P. Grandjean, P. J. Landrigan, *Lancet Neurol.* 13, 330 (March, 2014).
4. L. L. Needham et al., *Environ. Sci. Technol.* 45, 1121 (February, 2011).
5. P. Grandjean, P. J. Landrigan, *Lancet* 368, 2167 (December, 2006).
6. D. C. Bellinger, *Environ. Health Perspect.* 120, 501 (April, 2012).
7. Z. G. Hou et al., *Stem Cell Res. Ther.* 4, S12 (December, 2013).
8. D. V. Hansen et al., *Nat. Neurosci.* 16, 1576 (November, 2013).
9. J. H. Lui, D. V. Hansen, A. R. Kriegstein, *Cell* 146, 18 (July, 2011).

10. P. Rakic, *Nat. Rev. Neurosci.* 10, 724 (October, 2009).
11. I. Bystron, C. Blakemore, P. Rakic, *Nat. Rev. Neurosci.* 9, 110 (February, 2008).
12. M. Marin-Padilla, Front. *Neuroanat.* 6, (September, 2012).
13. M. Marin-Padilla, D. S. Knopman, *J. Neuropathol. Exp. Neurol.* 70, 1060 (December, 2011).
14. J. M. James, Y.-s. Mukouyama, *Semin. Cell Dev. Biol.* 22, 1019 (2011).
15. H. Stolp, A. Neuhaus, R. Sundramoorthi, Z. Molnar, *Front. Psychiatry* 3, (2012).
16. F. Ginhoux, S. Lim, G. Hoeffel, D. Low, T. Huber, *Front. Cell. Neurosci.* 7, (April, 2013).
17. T. Arnold, C. Betsholtz, *Vascular Cell* 5, 4 (2013).
18. H. Kettenmann, U. K. Hanisch, M. Noda, A. Verkhratsky, *Physiol. Rev.* 91, 461 (April, 2011).
19. C. Verney, A. Monier, C. Fallet-Bianco, P. Gressens, *J. Anat.* 217, 436 (October, 2010).
20. A. Monier et al., *J. Neuropathol. Exp. Neurol.* 66, 372 (May, 2007).
21. A. Monier, P. Evrard, P. Gressens, C. Verney, *J. Comp. Neurol.* 499, 565 (December, 2006).
22. J. A. Thomson et al., *Science* 282, 1145 (November, 1998).
23. J. Y. Yu et al., *Science* 318, 1917 (December, 2007).
24. K. Takahashi et al., *Cell* 131, 861 (November, 2007).
25. S. C. Zhang, M. Wernig, I. D. Duncan, O. Brustle, J. A. Thomson, *Nat. Biotechnol.* 19, 1129 (December, 2001).
26. O. Brustle et al., *Science* 285, 754 (Jul. 30, 1999).
27. M. A. Lancaster et al., *Nature* 501, 373 (September, 2013).
28. J. Mariani et al., *Proceedings of the National Academy of Sciences* 109, 12770 (Jul. 31, 2012, 2012).
29. M. Eiraku et al., *Cell Stem Cell* 3, 519 (November, 2008).
30. M. Ader, E. M. Tanaka, *Curr. Opin. Cell Biol.* 31, 23 (2014).
31. I. Singec et al., *Nat. Methods* 3, 801 (October, 2006).
32. B. D. Fairbanks et al., *Adv. Mater.* 21:5005-5010 (December, 2009).
33. M. Marin-Padilla, *Front. Neuroanat.* 6, (2012 Sep. 13, 2012).
34. P. Rakic, *Cereb. Cortex* 13, 541 (June, 2003).
35. I. Bystron, P. Rakic, Z. Molnar, C. Blakemore, *Nat Neurosci* 9, 880 (2006).
36. G. Meyer, J. P. Schaaps, L. Moreau, A. M. Goffinet, *J Neurosci.* 20, 1858 (March, 2000).
37. N. Zecevic, A. Milosevic, S. Rakic, M. Marin-Padilla, *The Journal of Comparative Neurology* 412, 241 (1999).
38. M. H. Dominguez, A. E. Ayoub, P. Rakic, *Cereb. Cortex* 23, 2632 (November, 2013).
39. B. J. Molyneaux, P. Arlotta, J. R. L. Menezes, J. D. Macklis, *Nat. Rev. Neurosci.* 8, 427 (June, 2007).
40. J. Struyf, S. Dobrin, D. Page, *BMC Genomics* 9, (November, 2008).
41. T. R. Golub et al., *Science* 286, 531 (October, 1999).
42. V. N. Vapnik, *Statistical Learning Theory*. (Wiley, New York, 1998), pp. 736.
43. C. Cortes, V. Vapnik, *Mach. Learn.* 20, 273 (September, 1995).
44. T. S. Furey et al., *Bioinformatics* 16, 906 (October, 2000).
45. M. Moors et al., *Environ. Health Perspect.* 117, 1131 (July, 2009).
46. N. C. Kleinstreuer et al., *Nat. Biotechnol.* 32, 583 (June, 2014).
47. M. S. Wilson, J. R. Graham, A. J. Ball, *Neurotoxicology* 42, 33 (May, 2014).
48. N. V. Balmer, M. Leist, *Basic Clin. Pharmacol. Toxicol.* 115, 59 (July, 2014).
49. H. Olson et al., *Regulatory Toxicology and Pharmacology* 32, 56 (2000).
50. S. Rakic, N. Zecevic, *Cereb. Cortex* 13, 1072 (October, 2003).
51. T. Kadoshima et al., *Proc. Natl. Acad. Sci. U.S.A* 110, 20284 (December, 2013).
52. G. K. Chen et al., *Nat. Methods* 8, 424 (May, 2011).
53. X. J. Li et al., *Development* 136, 4055 (December, 2009).
54. S. M. Chambers et al., *Nat. Biotechnol.* 27, 275 (March, 2009).
55. H. Nagase, G. B. Fields, *Biopolymers* 40, 399 (1996).
56. M. D. Pierschbacher, E. Ruoslahti, *Nature* 309, 30 (1984).
57. B. Langmead, C. Trapnell, M. Pop, S. L. Salzberg, *Genome Biol* 10, R25 (2009).
58. B. Li, C. N. Dewey, *BMC Bioinformatics* 12, 323 (2011).

We claim:

1. A method of making a composition comprising human microglial cells, the method comprising culturing human pluripotent stem cell-derived CD45$^+$/CD11b$^+$/CD14$^+$ primitive macrophages for at least five days in a chemically defined hydrogel-based three-dimensional tissue construct comprising stratified layers of human neurons and glia, thereby producing a composition comprising human microglial cells expressing CD68, CD11b, Triggering Receptor Expressed on Myeloid Cells 2 (TREM2), and Ionized calcium-binding adapter molecule 1 (Iba1).

2. The method of claim 1, wherein the primitive macrophages are obtained by culturing human myeloid progenitors in the presence of a culture medium comprising insulin and a hematopoietic cytokine, whereby the cultured myeloid progenitors differentiate into a cell population comprising at least 80% CD45$^+$/CD11b$^+$/CD14$^+$ primitive macrophages, wherein the human myeloid progenitors are obtained by
   (a) culturing human pluripotent stem cells under normoxic conditions for about 24 hours, wherein the pluripotent stem cells are cultured on a substrate comprising recombinant human Tenascin-C and in the presence of a culture medium consisting essentially of L-ascorbic acid-2-phosphate magnesium, sodium selenium, transferrin, insulin, NaHCO$_3$, fibroblast growth factor 2 (FGF2), transforming growth factor beta 1 (TGF($\alpha$1), and a Rho kinase (ROCK) inhibitor, whereby the cultured pluripotent stem cells differentiate into hematopoietic precursor cells (HPCs); and
   (b) culturing the HPCs obtained in (a) for about 3 to about 5 days in a culture medium comprising FGF2, a vascular endothelium growth factor (VEGF), thrombopoietin (TPO), stem cell factor (SCF), interleukin-6 (IL-6), and interleukin-3 (IL-3), wherein the hematopoietic progenitor cells differentiate into myeloid progenitors.

3. The method of claim 1, wherein, prior to the contacting step, the human primitive macrophages are cultured for about 5 days in a culture medium consisting essentially of Iscove's Modified Dulbecco's Media (IMDM), interleukin-1-beta (IL-1$\alpha$), serum, and a hematopoietic growth factor.

4. The method of claim 1, wherein the hematopoietic growth factor is macrophage colony-stimulating factor (M-CSF).

5. A method of producing human microglial cells, wherein the method comprises culturing human pluripotent stem cell-derived CD45$^+$/CD11b$^+$/CD14$^+$ primitive macrophages for at least five days in a chemically defined culture medium comprising Iscove's Modified Dulbecco's Media (IMDM), interleukin-1-beta (IL-1$\alpha$), serum, and a hematopoietic growth factor, whereby a cell population comprising human microglial cells expressing CD68, CD11b, Triggering Receptor Expressed on Myeloid Cells 2 (TREM2), and Ionized calcium-binding adapter molecule 1 (Iba1) is produced.

6. The method of claim 5, wherein the chemically defined culture medium consists essentially of IMDM, IL-1$\alpha$, serum, and macrophage colony-stimulating factor (M-CSF).

7. The method of claim 5, wherein the primitive macrophages are obtained by culturing human myeloid progenitors in the presence of a culture medium comprising insulin and a hematopoietic cytokine, whereby the cultured myeloid progenitors differentiate into a cell population comprising at least 80% CD45$^+$/CD11b$^+$/CD14$^+$ primitive macrophages, wherein the human myeloid progenitors are obtained by
   (a) culturing human pluripotent stem cells under normoxic conditions for about 24 hours, wherein the pluripotent stem cells are cultured on a substrate comprising recombinant human Tenascin-C and in the presence of a culture medium consisting essentially of L-ascorbic acid-2-phosphate magnesium, sodium selenium, transferrin, insulin, NaHCO$_3$, fibroblast growth factor 2 (FGF2), transforming growth factor beta 1 (TGF$\alpha$1), and a Rho kinase (ROCK) inhibitor, whereby the cultured pluripotent stem cells differentiate into hematopoietic precursor cells (HPCs); and
   (b) culturing the HPCs obtained in (a) for about 3 to about 5 days in a culture medium comprising FGF2, a vascular endothelium growth factor (VEGF), thrombopoietin (TPO), stem cell factor (SCF), interleukin-6 (IL-6), and interleukin-3 (IL-3), wherein the hematopoietic progenitor cells differentiate into myeloid progenitors.

* * * * *

SEQUENCE LISTING

<160> NUMBER OF SEQ ID NOS: 2

<210> SEQ ID NO 1
<211> LENGTH: 12
<212> TYPE: PRT
<213> ORGANISM: Artificial Sequence
<220> FEATURE:
<223> OTHER INFORMATION: synthetic

<400> SEQUENCE: 1

Lys Cys Gly Pro Gln Gly Ile Trp Gly Gln Cys Lys
1               5                   10

<210> SEQ ID NO 2
<211> LENGTH: 5
<212> TYPE: PRT
<213> ORGANISM: Artificial Sequence
<220> FEATURE:
<223> OTHER INFORMATION: synthetic

```
<400> SEQUENCE: 2

Cys Arg Gly Asp Ser
1               5
```